(12) United States Patent
Xu et al.

(10) Patent No.: US 10,697,022 B2
(45) Date of Patent: Jun. 30, 2020

(54) PIK3CA NOVEL MUTATIONS DETECTION FOR DIAGNOSIS OF ACQUIRED CETUXIMAB RESISTANCE IN METASTATIC COLORECTAL CANCER PATIENTS

(71) Applicant: AFFILIATED HOSPITAL, ACADEMY OF MILITARY MEDICAL SCIENCES, Beijing (CN)

(72) Inventors: Jianming Xu, Beijing (CN); Yan Wang, Beijing (CN); Yan Wang, Beijing (CN)

(73) Assignee: AFFILIATED HOSPITAL, ACADEMY OF MILITARY MEDICAL SCIENCES, Beijing (CN)

( * ) Notice: Subject to any disclaimer, the term of this patent is extended or adjusted under 35 U.S.C. 154(b) by 439 days.

(21) Appl. No.: 15/525,922

(22) PCT Filed: Nov. 6, 2015

(86) PCT No.: PCT/CN2015/093963
§ 371 (c)(1),
(2) Date: Sep. 25, 2017

(87) PCT Pub. No.: WO2016/074589
PCT Pub. Date: May 19, 2016

(65) Prior Publication Data
US 2018/0016640 A1 Jan. 18, 2018

(30) Foreign Application Priority Data

Nov. 10, 2014 (CN) .......................... 2014 1 0645282
Dec. 16, 2014 (CN) .......................... 2014 1 0779781

(51) Int. Cl.
*C12P 19/34* (2006.01)
*C12Q 1/6886* (2018.01)
*C12Q 1/68* (2018.01)

(52) U.S. Cl.
CPC ............ *C12Q 1/6886* (2013.01); *C12Q 1/68* (2013.01); *C12Y 207/01153* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| 8,026,053 B2 * | 9/2011 | Samuels | C12Q 1/6886 435/6.14 |
| 2011/0166029 A1 * | 7/2011 | Margulies | C12Q 1/6883 506/7 |
| 2016/0201131 A1 * | 7/2016 | Wang | C12Q 1/6883 506/2 |

FOREIGN PATENT DOCUMENTS

| CN | 103324846 A | 9/2013 |
| CN | 104531854 A | 4/2015 |

OTHER PUBLICATIONS

Rychlik et al., Nucleic Acids Research 17(21), 8543-8551 (1989) (Year: 1989).*
Diaz JR., L. et al., "The molecular evolution of acquired resistance to targeted EGFR blockade in colorectal cancers," Nature, vol. 486, No. 7404, Jun. 28, 2012, Published Online Jun. 13, 2012, 10 pages.
Chaft, J. et al., "Coexistence of PIK3CA and Other Oncogene Mutations in Lung Adenocarcinoma-Rationale for Comprehensive Mutation Profiling," Molecular Cancer Therapeutics, vol. 11, No. 2, Feb. 2012, 8 pages.
Liu, H. et al., "Relationaship Among PIK3CA Mutation, PTEN Expressions, and Efficacy of Cetuximab in Colorectal Cancer," Science and Technology Review, vol. 30, No. 16, Jun. 8, 2012, 5 pages. (Englsih Abstract p. 1).
ISA State Intellectual Property Office of the People's Republic of China, International Search Report Issued in Application No. PCT/CN2015/093963, dated Feb. 15, 2016, WIPO, 6 pages.

* cited by examiner

*Primary Examiner* — Kenneth R Horlick
(74) *Attorney, Agent, or Firm* — McCoy Russell LLP

(57) ABSTRACT

Disclosed is a kit for detecting drug resistance of cetuximab in the treatment of metastatic colorectal cancer. The kit comprises a substance used for detecting gene mutations in Exon 19 of the PIK3CA gene, and may further comprise a specification recording the following contents: if Exon 19 in the PIK3CA gene of a patient with metastatic colorectal cancer as a subject to be tested, who is intended to receive cetuximab treatment or is receiving cetuximab treatment and does not have drug resistance, has at least one of K944N, F930S, V955G, V955I, and K966E mutations, the subject to be tested will develop drug resistance or will be a candidate to develop drug resistance when receiving or continuing to receive cetuximab for treating metastatic colorectal cancer.

2 Claims, 3 Drawing Sheets
Specification includes a Sequence Listing.

PIK3CA NOVEL MUTATIONS DETECTION FOR DIAGNOSIS OF ACQUIRED CETUXIMAB RESISTANCE IN METASTATIC COLORECTAL CANCER PATIENTS

CROSS-REFERENCE TO RELATED APPLICATIONS

The present application is a U.S. National Phase of International Patent Application Serial No. PCT/CN2015/093963 entitled "KIT FOR DETECTING DRUG RESISTANCE OF CETUXIMAB USED FOR METSTIC COLORECTAL CANCER TREATMENT," filed on Nov. 6, 2015. International Patent Application Serial No. PCT/CN2015/093963 claims priority to Chinese Patent Application No. 201410645282.0 filed on Nov. 10, 2014; and to Chinese Patent Application No. 201410779781.9 filed on Dec. 16, 2014. The entire contents of each of the above-referenced applications are hereby incorporated by reference for all purposes.

INCORPORATION BY REFERENCE OF ELECTRONICALLY SUBMITTED MATERIAL

Incorporated by reference in its entirety herein is a computer-readable nucleotide sequence listing submitted herewith and identified as follows: 20,415 bytes ASCII (Text) file named "Substitute_Sequence_Listing_JEE17307-PCTUS," created Oct. 13, 2017.

TECHNICAL FIELD

The present invention belongs to the field of bio-medicine, and relates to a kit for detecting drug resistance of cetuximab in the treatment of metastatic colorectal cancer and the uses thereof.

BACKGROUND ART

Although there are great differences in the morbidity and mortality of colorectal cancer all over the world, in most developed countries, colorectal cancer is always the third cause of cancer-related death. The monoclonal antibodies targeting Epidermal Growth Factor Receptor (EGFR), such as cetuximab, panitumumab, can significantly improve the survivals of patients in the treatments of patients with RAS wild-type metastatic colorectal cancers (mCRCs), thus they are recommended for the treatments of RAS wild-type mCRCs. Currently, although RAS gene detection has been used as a conventional detection of selecting EGFR monoclonal antibodies for the patients, the treatments of EGFR monoclonal antibodies are ineffective for 30-40% of RAS wild-type patients. More importantly, the majority of RAS wild-type patients will still develop drug resistance after receiving the treatments of EGFR monoclonal antibodies. Therefore, it is of great significance for the instruction of the clinic applications of EGFR monoclonal antibodies to timely monitor the occurrence of drug resistance before the treatment is confirmed as ineffective by imageology, so as to avoid unnecessarily prolonged ineffective treatment.

Recent studies reported that a series of genes downstream of EGFR signal pathway, such as BRAF, PIK3CA and PTEN, may relate to the drug resistance of EGFR monoclonal antibodies. However, several studies obtained contradictory conclusions, and in the studies related to drug resistance, the traditional method is to focus on the somatic mutations which have existed in tumor tissues before the treatments, and to monitor their changes during the process of treatments, but such strategy may ignore new mutations occurring during the process of treatments, resulting in being unable to sufficiently assess the gene mutations related to drug resistance.

SUMMARY OF THE INVENTION

One purpose of the present invention is to provide a kit for detecting or assisting in detecting drug resistance of cetuximab in the treatment of metastatic colorectal cancer.

The kit for detecting or assisting in detecting drug resistance of cetuximab in the treatment of metastatic colorectal cancer provided by the present invention specifically comprises a substance used for detecting whether the Exon 19 in PIK3CA gene has a gene mutation or not.

The kit may also comprise a specification recording the following contents:

if the Exon 19 in PIK3CA gene of a patient with metastatic colorectal cancer as a subject to be tested, who is intended to receive cetuximab treatment or is receiving cetuximab treatment and does not develop drug resistance, has at least one of following (a)-(e) mutations, the subject to be tested will develop drug resistance or will be a candidate that develops drug resistance when receiving or continuing to receive cetuximab for treating metastatic colorectal cancer:

(a) Lysine at the 944th amino acid of the PIK3CA gene coding protein mutates into Asparagine (K944N);
 (b) Phenylalanine at 930th amino acid of the PIK3CA gene coding protein mutates into Serine (F930S);
 (c) Valine at the 955th amino acid of the PIK3CA gene coding protein mutates into Isoleucine (V955I);
 (d) Valine at the 955th amino acid of the PIK3CA gene coding protein mutates into Glycine (V955G); and
 (e) Lysine at the 966th amino acid of the PIK3CA gene coding protein mutates into Glutamic Acid (K966E).

In the present invention, the above each mutation corresponds to gene level, and is specifically embodied as:
 the (a) is A at Position 48 in the Exon 19 of the PIK3CA gene mutates into T;
 the (b) is Tat Position 5 in the Exon 19 of the PIK3CA gene mutates into C;
 the (c) is G at Position 79 in the Exon 19 of the PIK3CA gene mutates into A;
 the (d) is Tat Position 80 in the Exon 19 of the PIK3CA gene mutates into G; and
 the (e) is A at Position 112 in the Exon 19 of the PIK3CA gene mutates into G.

Where, the nucleotide sequence of the Exon 19 in the PIK3CA gene (wild-type) is shown as SEQ ID NO: 1 in the Sequence List.

The use of the substance used for detecting whether the Exon 19 in PIK3CA gene has a gene mutation or not for manufacturing a kit for detecting or assisting in detecting drug resistance of cetuximab in the treatment of metastatic colorectal cancer also belongs to the protection scope of the present invention.

In the use, the gene mutations of the Exon 19 in the PIK3CA gene are at least one of:
 (a) Lysine at the 944th amino acid of the PIK3CA gene coding protein mutates into Asparagine (K944N);
 (b) Phenylalanine at 930th amino acid of the PIK3CA gene coding protein mutates into Serine (F930S);
 (c) Valine at the 955th amino acid of the PIK3CA gene coding protein mutates into Isoleucine (V955I);

(d) Valine at the 955th amino acid of the PIK3CA gene coding protein mutates into Glycine (V955G); and
(e) Lysine at the 966th amino acid of the PIK3CA gene coding protein mutates into Glutamic Acid (K966E).

In the present invention, the above each mutation corresponds to gene level, and is specifically embodied as:
the (a) is A at Position 48 in the Exon 19 of the PIK3CA gene mutates into T;
the (b) is Tat Position 5 in the Exon 19 of the PIK3CA gene mutates into C;
the (c) is G at Position 79 in the Exon 19 of the PIK3CA gene mutates into A;
the (d) is T at Position 80 in the Exon 19 of the PIK3CA gene mutates into G; and
the (e) is A at Position 112 in the Exon 19 of the PIK3CA gene mutates into G.

Where, the nucleotide sequence of the Exon 19 in the PIK3CA gene (wild-type) is shown as SEQ ID NO: 1 in the Sequence List.

The use of the substance used for detecting whether the Exon 19 in PIK3CA gene has a gene mutation or not for detecting or assisting in detecting drug resistance of cetuximab in the treatment of metastatic colorectal cancer also belongs to the protection scope of the present invention.

In the use, the gene mutations of the Exon 19 in the PIK3CA gene are at least one of:
(a) Lysine at the 944th amino acid of the PIK3CA gene coding protein mutates into Asparagine (K944N);
(b) Phenylalanine at 930th amino acid of the PIK3CA gene coding protein mutates into Serine (F930S);
(c) Valine at the 955th amino acid of the PIK3CA gene coding protein mutates into Isoleucine (V955I);
(d) Valine at the 955th amino acid of the PIK3CA gene coding protein mutates into Glycine (V955G); and
(e) Lysine at the 966th amino acid of the PIK3CA gene coding protein mutates into Glutamic Acid (K966E).

In the use, if the Exon 19 in PIK3CA gene of a patient with metastatic colorectal cancer as a subject to be tested, who is intended to receive cetuximab treatment or is receiving cetuximab treatment and does not develop drug resistance, has at least one of the (a)-(e) mutations, the subject to be tested will develop drug resistance or will be a candidate that develops drug resistance when receiving or continuing to receive cetuximab for treating metastatic colorectal cancer.

In the present invention, the above each mutation corresponds to gene level, and is specifically embodied as:
the (a) is A at Position 48 in the Exon 19 of the PIK3CA gene mutates into T;
the (b) is Tat Position 5 in the Exon 19 of the PIK3CA gene mutates into C;
the (c) is G at Position 79 in the Exon 19 of the PIK3CA gene mutates into A;
the (d) is Tat Position 80 in the Exon 19 of the PIK3CA gene mutates into G; and
the (e) is A at Position 112 in the Exon 19 of the PIK3CA gene mutates into G.

Where, the nucleotide sequence of the Exon 19 in the PIK3CA gene (wild-type) is shown as SEQ ID NO: 1 in the Sequence List.

In the kit or the use, the substance used for detecting whether the Exon 19 in PIK3CA gene has a gene mutation or not is Primer Pair 1 and/or Primer Pair 2.

The Primer Pair 1 is a primer pair composed of two single stranded DNA molecules shown by SEQ ID NO: 2 and SEQ ID NO: 3 in the Sequence List; and the Primer Pair 2 is a primer pair composed of two single stranded DNA molecules shown by SEQ ID NO: 4 and SEQ ID NO: 5 in the Sequence List.

BEST MODES OF THE INVENTION

Figure 1:
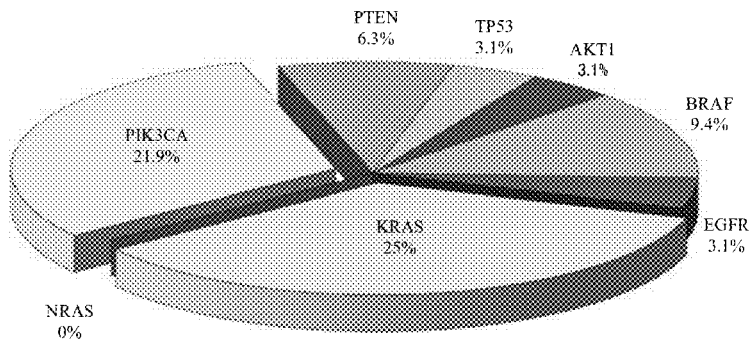
FIG. 1 is the distributions of drug resistance-related mutations of ctDNA in each gene.

The following Examples are convenient for better understanding the present invention, but do not limit the present invention. Unless otherwise specified, the experimental methods in the following Examples are all conventional methods. Unless otherwise specified, the experimental materials in the following Examples are all purchased from conventional Biochemical Reagent Stores. The quantitative tests in the following Examples are all repeated three times, and the results are averaged.

Example 1, Screening and Confirmation of Gene Mutations in Circulating Tumor DNA (ctDNA) of the Metastatic Colorectal Cancer Patients Who Develop Drug Resistance in the Treatment with Cetuximab I, Patients to be Tested and the Collection of Study Samples The selected patients have metastatic colorectal cancers confirmed by pathology, KRAS 12th and 13th codons and BRAF V600E of the tumor tissue are all detected as wild-types via direct sequencing before treatment, and the patients are suitable for receiving cetuximab±chemotherapy. These patients complete at least 4-6 weeks of cetuximab±chemotherapy treatments, the tumor sizes are assessed through CT examination and in a double-blind mode, and the therapeutic effects are evaluated with RECIST 1.1. Before treatment, the tumor tissues and complete blood cells of the patients to be tested are collected for analyzing tumor-related gene mutations, while a series of plasma samples of the patients before treatment, during treatment, and after occurrence of drug resistance are collected to analyze the dynamic changes of tumor-related gene mutations in ctDNA. All of the patients signed informed consents. If progression free survival (PFS)≥6 weeks, the patients are considered as secondary resistant patients, and if PFS<6 weeks, the patients are primary resistant. Firstly, drug resistance-related gene mutations are screened in a total of 32 secondary resistant patients, and are then verified in 12 primary resistant patients whether these mutations are related to primary drug resistance or not. In 32 secondary patients to be tested, for a total of 20 patients, 133 plasma samples at a series of time points during treatment (every 4 weeks) are collected, and for other 12 patients, a total of 30 plasma samples comprising at least 2-3 time points before treatment and after progressive disease (PD). For 12 primary resistant patients, a total of 26 plasma samples before and/or after treatment are collected.

II, Screening and Confirmation of Gene Mutations in Circulating Tumor DNA (ctDNA)

1, Sample Treatment and Amplicon Sequencing

DNA from tumor tissues, complete blood cells and plasma samples is extracted and quantified, and an amplicon deep-sequencing is performed on the following target genes: NRAS gene (Exons 2, 3, and 4), KRAS gene (Exons 2, 3, and 4), BRAF gene (Exon 15), PIK3C gene (Exons 8 and 19), AKT1 gene (Exon 3), TP53 gene (Exons 5, 6, and 7), PTEN gene (Exons 5, 7, and 8) and EGFR gene (Exons 10 and 12). For PIK3CA gene, as it is found in the prior studies that the hotspot mutations in Exons 9 and 20 are not related to the drug resistance of EGFR monoclonal antibodies, Exons 8 and 19 are selected to detect in the present invention. Exon 8 encodes partial cell membrane-bound region, and Exon 19 is similar to Exon 20, which encode partial activation loop and ATP binding pocket. Similar to hotspot mutation, these partial mutations of PIC3CA will also result in the structural activation of enzymes.

The amplicon primers are designed with respect to target gene fragments, and a total of 41 pairs of primers (see Table 1) are divided into 2 primer pools. The PCR amplification is performed by loading 10 ng DNA, and the construction of amplicon library is completed via end repair, ligation (adding linker), and PCR amplification. After purification and quantification, the fragment lengths and concentrations are determined by capillary electrophoresis employing 2100 Bioanalyzer (Agilent Company), and finally the products for constructing library are uniformly diluted to 26 pM and sequenced on the machine. The sequencing is performed with Ion Proton platform (Cat No. 4476610, Ion PI Sequencing 200 Kit v3 Cat No. 4488315) or PGM platform (Cat No. 4462921, Ion 318 ™ Chip Kit Cat No. 4466617) of Proton System of Life Company. The sequencing depths in tumor tissues and complete blood cells are 1000×, and those in plasma samples are 10000×.

TABLE 1

Amplicon Primer Sequences with respect to Different Target Gene Fragments

| Amplicons | Forward Primers (5'-3') | Reverse Primers (5'-3') |
| --- | --- | --- |
| AKT1-exon 3 | CCCCCAAATCTGAATCCCGAG<br>SEQ ID NO: 6 | CTCCTCAAGAATGATGGCACCTT<br>SEQ ID NO: 7 |
| AKT1-exon 3 | GCCGCTCCTTGTAGCCAAT<br>SEQ ID NO: 8 | GGGTCTGACGGGTAGAGTGT<br>SEQ ID NO: 9 |
| BRAF-exon 15 | CATCCACAAAATGGATCCAGACAAC<br>SEQ ID NO: 10 | GCTTGCTCTGATAGGAAAATGAGAT<br>SEQ ID NO: 11 |
| BRAF-exon 15 | GTTGAGACCTTCAATGACTTTCTAGTAA<br>SEQ ID NO: 12 | GTGGGTCCCATCAGTTTGAACA<br>SEQ ID NO: 13 |
| EGFR-exon 10 | ACCTCCATCAGTGGCGATCT<br>SEQ ID NO: 14 | CAGAGGAGGAGTATGTGTGAAGGA<br>SEQ ID NO: 15 |
| EGFR-exon 10 | CACCCTGTTGTTTGTTTCAGTGAC<br>SEQ ID NO: 16 | AACAGGAAATATGTCGAAAAGTTCTCT<br>SEQ ID NO: 17 |
| EGFR-exon 12 | GTCAATCAAAGGTGGTCTGGAGAA<br>SEQ ID NO: 18 | AGGGAGCGTAATCCCAAGGA<br>SEQ ID NO: 19 |
| EGFR-exon 12 | GTGCTATGCAAATACAATAAACTGGAAA<br>SEQ ID NO: 20 | ACAAATAAAGGACCCATTAGAACCAACTC<br>SEQ ID NO: 21 |

TABLE 1 -continued

Amplicon Primer Sequences with respect to Different Target Gene Fragments

| Amplicons | Forward Primers (5'-3') | Reverse Primers (5'-3') |
|---|---|---|
| EGFR-exon 12 | CAGTCGTCAGCCTGAACATAACA<br>SEQ ID NO: 22 | CTGACCGGAGGTCCCAAAC<br>SEQ ID NO: 23 |
| KRAS-exon 2 | CCAGCTCCAACTACCACAAGT<br>SEQ ID NO: 24 | CTGGTGGAGTATTTGATAGTGTATTAACCTT<br>SEQ ID NO: 25 |
| KRAS-exon 2 | AAAGAATGGTCCTGCACCAGTAA<br>SEQ ID NO: 26 | AGGCCTGCTGAAAATGACTGAATATAA<br>SEQ ID NO: 27 |
| KRAS-exon 3 | GAAAGCCCTCCCCAGTCC<br>SEQ ID NO: 28 | TGCACTGTAATAATCCAGACTGTGTTT<br>SEQ ID NO: 29 |
| KRAS-exon 3 | AATGTCAGCTTATTATATTCAATTTAAACCCAC<br>SEQ ID NO: 30 | GCAATGAGGGACCAGTACATGA<br>SEQ ID NO: 31 |
| KRAS-exon 4 | ACTGTTCTAGAAGGCAAATCACATTTA<br>SEQ ID NO: 32 | GTGGACAGGTTTTGAAAGATATTTGTGT<br>SEQ ID NO: 33 |
| KRAS-exon 4 | AATGACATAACAGTTATGATTTTGCAGAAAA<br>SEQ ID NO: 34 | CAGGCTCAGGACTTAGCAAGAAG<br>SEQ ID NO: 35 |
| KRAS-exon 4 | CTTTGCTGATGTTTCAATAAAAGGAATTCCA<br>SEQ ID NO: 36 | GACTCTGAAGATGTACCTATGGTCCTA<br>SEQ ID NO: 37 |
| NRAS-exon 2 | TCACCTCTATGGTGGGATCATATTCA<br>SEQ ID NO: 38 | ACCCTGATTACTGGTTTCCAACAG<br>SEQ ID NO: 39 |
| NRAS-exon 2 | AAATAACTTTTTACTTTCTCTCCTCTTATTCCT<br>SEQ ID NO: 40 | CAGCTAATCCAGAACCACTTTGTAGA<br>SEQ ID NO: 41 |
| NRAS-exon 3 | AAAAGCTCTATCTTCCCTAGTGTGGTA<br>SEQ ID NO: 42 | GCTTCCTCTGTGTATTTGCCATCAATAA<br>SEQ ID NO: 43 |
| NRAS-exon 3 | TCTTCTTGTCCAGCTGTATCCAGTAT<br>SEQ ID NO: 44 | AAAAATTGAACTTCCCTCCCTCC<br>SEQ ID NO: 45 |
| NRAS-exon 3 | AGGTTAATATCCGCAAATGACTTGCTA<br>SEQ ID NO: 46 | GATGGTGAAACCTGTTTGTTGGAC<br>SEQ ID NO: 47 |
| NRAS-exon 4 | GAATATGGATCACATCTCTACCAGAGTT<br>SEQ ID NO: 48 | GCCAAGAGTTACGGGATTCCATTC<br>SEQ ID NO: 49 |
| NRAS-exon 4 | TGGTCTTGGCTGAGGTTTCAAT<br>SEQ ID NO: 50 | TCCCGTTTTTAGGGAGCAGATTAAG<br>SEQ ID NO: 51 |
| PIK3CA-exon 8 | TTTTTATGGCAGTCAAACCTTCTCTCT<br>SEQ ID NO: 52 | CAGACCAATTGGCATGCTCTTC<br>SEQ ID NO: 53 |
| PIK3CA-exon 8 | GGTAAAGTTCCCAGATATGTCAGTGATT<br>SEQ ID NO: 54 | AATTGATACTTAATAAAACTCAGTGATTTGCCTT<br>SEQ ID NO: 55 |
| PIK3CA-exon 19 | ATTCAAGACATTTTGTATCTGCATATATCAAAC<br>(SEQ ID NO: 2) | GCACACGTTCTCGTTTATAACCAAATT<br>(SEQ ID NO: 3) |
| PIK3CA-exon 19 | GATTTTGGACACTTTTTGGATCACAAGA<br>(SEQ ID NO: 4) | GTGTTTTTAATTGCTCGAGCTCAC<br>(SEQ ID NO: 5) |
| PTEN-exon 5 | TGCAACATTTCTAAAGTTACCTACTTGT<br>SEQ ID NO: 56 | TGGTCAAGATCTTCACAAAAGGGTTT<br>SEQ ID NO: 57 |
| PTEN-exon 5 | GAAAGGGACGAACTGGTGTAATGAT<br>SEQ ID NO: 58 | ATAAATTCTCAGATCCAGGAAGAGGAAAG<br>SEQ ID NO: 59 |
| PTEN-exon 5 | TAACCCACCACAGCTAGAACTTATC<br>SEQ ID NO: 60 | TGCCCCGATGTAATAAATATGCACAT<br>SEQ ID NO: 61 |
| PTEN-exon 7 | CGACGGGAAGACAAGTTCATGTA<br>SEQ ID NO: 62 | TGTCCTTATTTTGGATATTTCTCCCAATG<br>SEQ ID NO: 63 |
| PTEN-exon 7 | GACAGTTAAAGGCATTTCCTGTGA<br>SEQ ID NO: 64 | GTAACGGCTGAGGGAACTCAAA<br>SEQ ID NO: 65 |
| PTEN-exon 8 | TCACTTTTGGGTAAATACATTCTTCATACCA<br>SEQ ID NO: 66 | ATATTCCTTGTCATTATCTGCACGC<br>SEQ ID NO: 67 |

TABLE 1 -continued

Amplicon Primer Sequences with respect to Different Target Gene Fragments

| Amplicons | Forward Primers (5'-3') | Reverse Primers (5'-3') |
|---|---|---|
| PTEN-exon 8 | AAGAAATCGATAGCATTTGCAGTATAGA<br>SEQ ID NO: 68 | TGGAGAAAAGTATCGGTTGGCTTT<br>SEQ ID NO: 69 |
| PTEN-exon 8 | TTGACTTTTTGCAAATGTTTAACATAGGT<br>SEQ ID NO: 70 | AGGTTTCCTCTGGTCCTGGTAT<br>SEQ ID NO: 71 |
| TP53-exon 5 | GCCACTGACAACCACCCTTAA<br>SEQ ID NO: 72 | GGAAGGAAATTTGCGTGTGGAGTA<br>SEQ ID NO: 73 |
| TP53-exon 5 | GTCGAAAAGTGTTTCTGTCATCCAAA<br>SEQ ID NO: 74 | CAGATAGCGATGGTGAGCAG<br>SEQ ID NO: 75 |
| TP53-exon 6 | GGGATGTGATGAGAGGTGGAT<br>SEQ ID NO: 76 | CCATCCTCACCATCATCACACTG<br>SEQ ID NO: 77 |
| TP53-exon 6 | GGCTCCTGACCTGGAGTCTT<br>SEQ ID NO: 78 | CATCTTGGGCCTGTGTTATCTCC<br>SEQ ID NO: 79 |
| TP53-exon 7 | CGCTTCTTGTCCTGCTTGCTTA<br>SEQ ID NO: 80 | TCCTATCCTGAGTAGTGGTAATCTACTG<br>SEQ ID NO: 81 |
| TP53-exon 7 | GCACCTCAAAGCTGTTCCGT<br>SEQ ID NO: 82 | CAAGGGTGGTTGGGAGTAGATG<br>SEQ ID NO: 83 |

2, Data Processing and Identification of Drug Resistance Mutations

The data generated by sequencing are filtered and quality screened, and unqualified fragments (including those in which fragment length is less than 50 bp, unique alignment rate <80%, PHRED quality score greater than 20) are removed. A single-end alignment is performed between the screened data and hg19 (Version GRCh37.p13) genomic data. Thereafter, the files in "bam" format generated during the process of alignment are input into SAM tool software to generate files in "mpileup" format. SNPs are then confirmed with VarScan.

The somatic mutations are determined by comparing SNVs in matched peripheral complete blood cells and paraffin samples of tumor tissues (FFPE).

The drug resistance-related candidate gene mutations are screened by employing the following steps: (1) the somatic mutations that only exist at progressive disease (PD) are screened using Varscan by comparing SNVs before treatment and after progressive disease (PD); (2) the mutation frequencies are ranked from low to high, and quartile values (Q1, Q2, Q3) and interquartile range (Qd=Q3–Q1) are calculated, all of the mutation frequencies ($M_f$) are then screened with the following equation: $M_f$–Q3>1.5Qd, and the mutations satisfying criteria are subjected to subsequent screening; and (3) the gene mutations, the frequencies of which are increased in the plasma samples at a series of time points, are selected. For the cases that do not reach PD when analyzed, the finally collected plasma samples are used as the samples of PD. The mutations are annotated with SNPnexus software. All of the non-synonymous mutations are further screened with two softwares, poly-phen 2.0 and SIFT, to determine the effects of mutations on protein functions.

3, Results

Eight genes, KRAS, NRAS, BRAF, PIK3CA, AKT1, PTEN, TP53, and EGFR, in EGFR signal pathway are selected, and a comprehensive gene mutation screening is performed on their 18 exons. The above genes are amplified from ctDNA and amplicon sequencing is performed, to find drug resistance-related new mutations occurring during the process of treatment. The average sequencing depth obtained in all amplicons of all patients is 9664×. Similar to the expectation, the majority of such mutations are low frequency mutations having a frequency lower than 0.5%. In order to facilitate subsequent mutation screening, the frequencies are not filtered when SNPs are acquired. For 20 patients having a series of plasma samples, the mutations of circulating DNAs before treatment and after PD are firstly compared. In the plasma samples of 11 cases at PD, average 26 mutations per case is found, and the frequencies are from 0.1% to 17.87%. Then, a quartile analysis is performed on these mutations to screen out the significantly increased mutations. Accordingly, a total of 16 non-synonymous mutations from 11 patients are screened out, average 1.5 mutations per case. The lowest frequency of these mutations is 0.97%, and the majority present rising trend in a series of plasma samples, which are used as drug resistance-related candidate gene mutations. Using such strategy, a total of 48 non-synonymous mutations are found in the plasma of a total of 32 secondary resistant patients as candidate gene mutations. Other than traditional research strategy, such mutation screening strategy is contributed to find the mutations that occur at a low frequency during the process of treatment, and present a significant rising trend.

The above mutations are further screened by using 2 prediction softwares for protein functions, PolyPhen-2 and SIFT, and "harmful" mutations judged by both softwares, hotspot mutations having known functions, and all PIK3CA mutations are selected as drug resistance-related mutations, which are used in subsequent function and clinic correlation analysis.

Via the above screening, 10 patients and a total of 14 mutations are found in 20 patients having plasma at a series of time points, and 8 patients and a total of 12 mutations are found in 12 patients having plasma at 2-3 time points before and after treatment. Therefore, in 32 secondary resistant patients subjected to mutation screening, a total of 26

(14+12) mutations are confirmed to be related to the drug resistance of cetuximab, wherein a total of 5 new mutations found on Exon 19 located in kinase catalytic domain of PIK3CA gene are related to drug resistance, which are F930S, K944N, V955G, V955I, K966E, respectively, and particularly, K944N gene is detected in 3 patients. Accordingly, the new mutations of PIK3CA gene occur in 21.9% (7/32) of secondary resistant patients, and KRAS mutations are detected in 25% (8/32) of secondary resistant patients, suggesting that PIK3CA gene mutation is an important reason resulting in cetuximab drug resistance in addition to KRAS. In addition, the inventors of the present invention also confirm 3 BRAF point mutations, including 1 V600E hotspot mutation. Furthermore, there are some sporadic gene mutations that are distributed in AKT1, EGFR and PTEN. The distributions of drug resistance-related mutations in ctDNA within each gene are specifically shown in FIG. 1.

Figure 2:
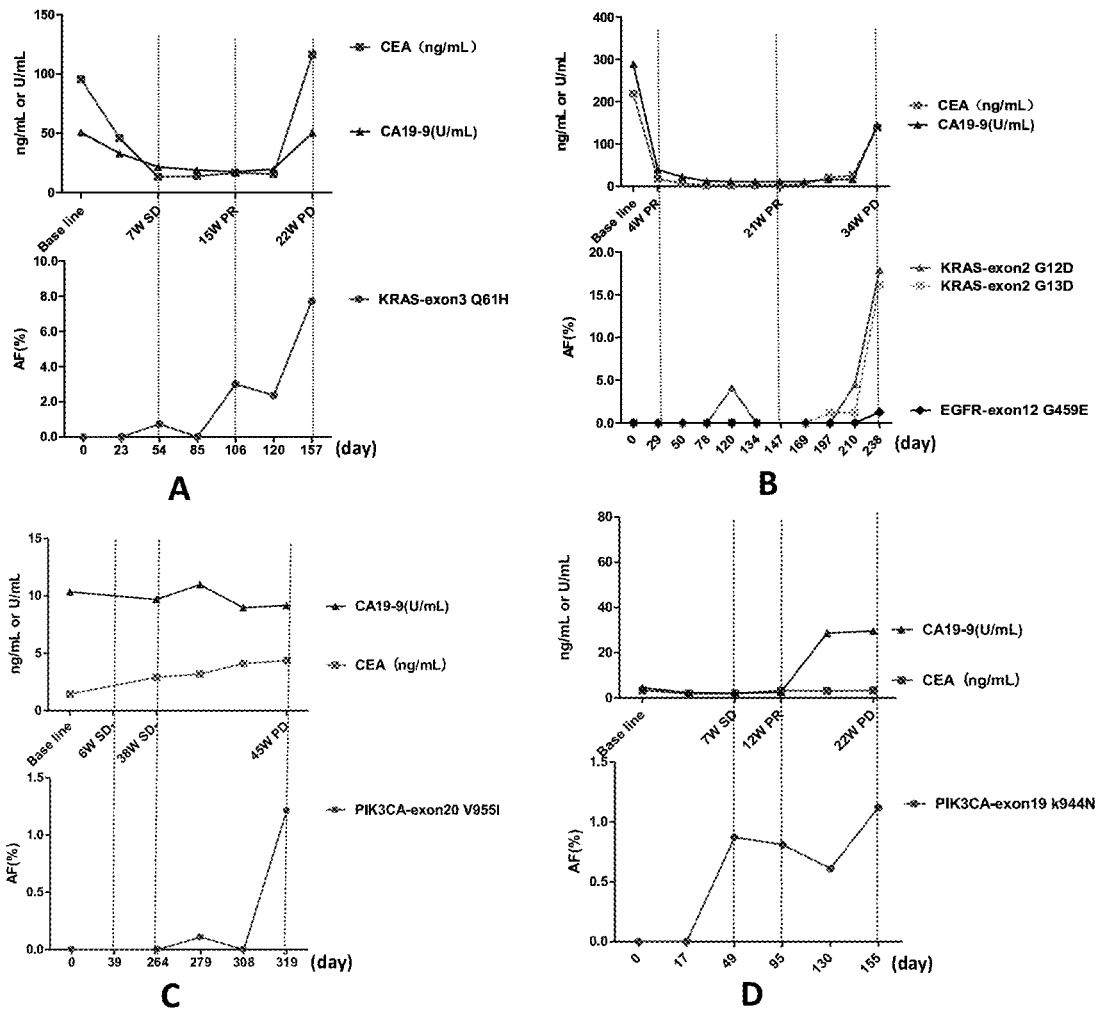
FIG. 2 is the comparisons between the gene mutation frequencies in ctDNA and the dynamic tendencies of therapeutic evaluations by imageology and tumor markers. A is NO. 2 patient; B is NO. 12 patient; C is NO. 7 patient; and D is NO. 17 patient. The upper portion of each figure represents the dynamic changes of the common tumor markers CEA (ng/ml), CA199 (U/ml) of colorectal cancer during the process of treatment, and the abscissa represents the results of therapeutic evaluations by imageology: Base line (pre-treatment); SD, stable disease; PR, partial remission (effective); and PD, progressive disease (drug resistance). The lower portion represents the dynamic changes of percentage of mutant genes detected in ctDNA, and the abscissa represents days from the beginning of the treatment, which is consistent with the abscissa of the upper portion in terms of time. AF: percentage of the mutant genes. Before the disease progression has been confirmed by imageology, mutant genes have occurred in ctDNA and present a rising trend.

III, Comparison of Frequencies of Drug Resistance-Related Mutations in ctDNA with the Dynamic Changes of CEA, CA19-9 and Tumor Imageology Evaluations For 10 patients having a series of plasma samples and in which secondary drug resistance-related mutations are detected, the present invention compares the frequencies of ctDNA mutant genes with the dynamic changes of CEA, CA19-9 and therapeutic evaluations by imageology (FIG. 2). As a result, PIK3CA gene mutations occur in NOs. 6, 7, 16, and 17 patients, KRAS gene mutations occur in NOs. 2, 12, 13, and 19 patients. Only 2 cases are other gene mutations: NO. 14 patient has V600E mutation of BRAF gene, and NO. 20 patient has Q245* (* represents terminator, amino acid sequence termination) mutation of PTEN gene. The mutation frequencies of the above genes present gradually increased tendency during the process of treatment, and the occurrence of mutations is about 10 weeks (4.0 weeks-18.1 weeks) earlier than drug resistance time evaluated by imageology.

IV, Protein Structure Modeling and Function Analysis for PIK3CA Mutant

1, Protein Structure Modeling and Analysis (1) Experimental Method

Protein homology modeling is performed using MODELLER software (Version 9v6). 4JPS three-dimensional structure in PDB database is used as template, and the three-dimensional structure models of PIK3CA wild-type and mutant-type that bind to PIK3R1 are established. The hydrogen atoms are added using CHARMM software (Version c32b2), and the interaction between amino acid residues is determined by one internal CHARMM script. VMD software (Version 1.9.1) is used for observing and analyzing modeling structure.

(2) Results

PIK3CA encodes catalytic subunit p110 of PI3K, which converts the substrate phosphatidylinositol-2-phosphate (PIP2) into phosphatidylinositol-3-phosphate (PIP3) by binding with regulatory subunit p85, and PIP3 can bind with the PH domain at N-terminal of protein kinase B (PKB, AKT), so as to activate AKT signal transduction pathway. Therefore, PIK3CA gene mutations play important role in the development and progression of tumors such as colorectal cancer, prostate cancer, breast cancer, ovarian cancer, liver cancer, lung cancer, melanoma and the like.

Figure 3:
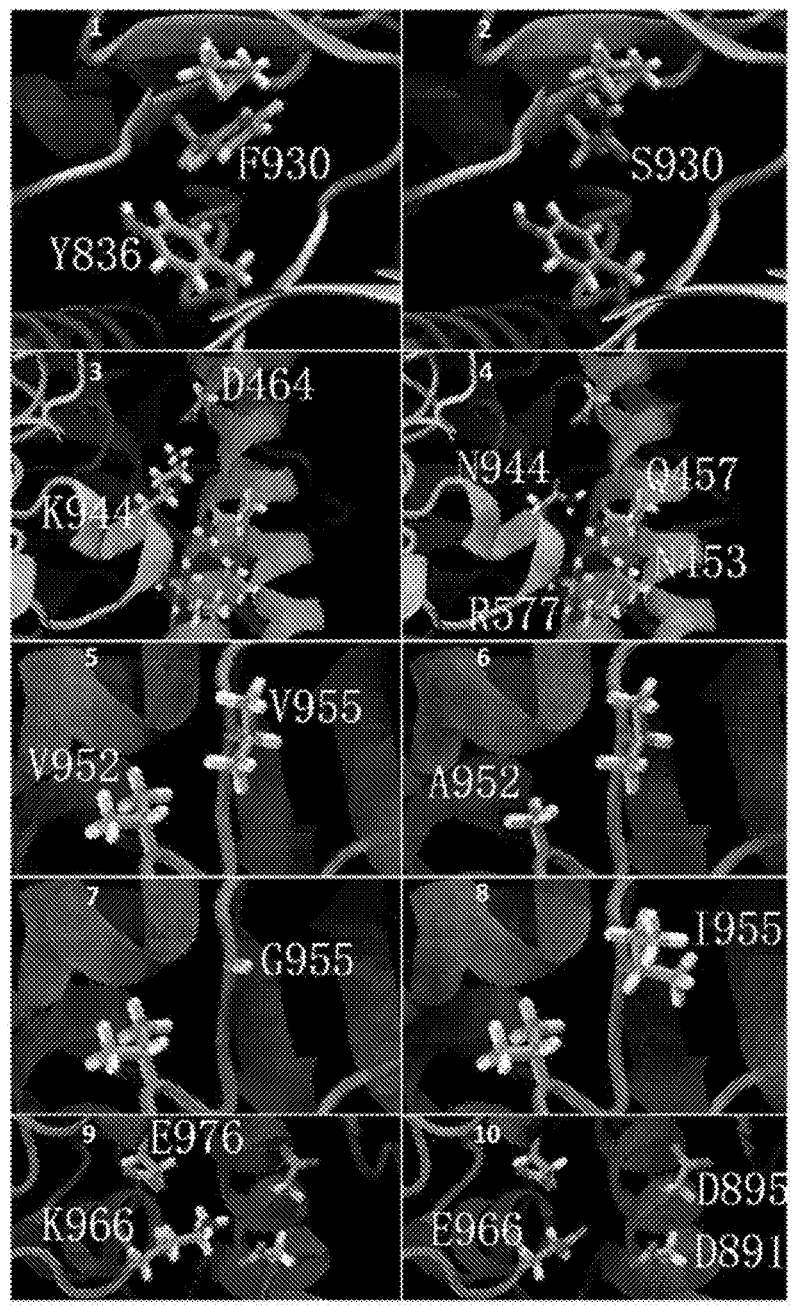
FIG. 3 is the protein structure modeling of PIK3CA mutant genes. 1, F930 side chain can form a π bond interaction with Tyr836 side chain; 2, after F930S mutation, this action disappears; 3, K944 side chain can form an acid-base attraction with D464 of a regulatory subunit; 4, after K944N mutation, this action disappears, and N944 side chain may form hydrogen bond interactions with N453, Q457, and R577 side chains of a regulatory subunit, which will cause a great conformational change of PIK3CA at this site; 5, both of V952 and V955 form hydrophobic side chains; 6, 7, both of V952A and V955G mutations diminish the hydrophobic side chains at the corresponding sites; 8, V955I mutation enlarges the hydrophobic side chain at the corresponding site; 9, the basic side chain of K966 may form acid-base attractions with the acidic side chains of E976, D891, and D895; and 10, after K966E mutation, the acid-base attraction in D1 becomes into an opposite repelling interaction.

Protein structure modeling is performed on PIK3CA using MODELLER software, and the effects of mutations on protein conformation are analyzed. PIK3CA mutations include 5 mutations (F930S, K944N, V955G, V955I, and K966E) found in ctDNA and 2 mutations (L938*, V952A) found in tumor tissues. 930 is located in ATP binding pocket, 944 and 955 are located in activation loop, and 966 is close to helical region that is closely related to the stability of main conformation raised at C-terminal of the kinase. The structural analysis shows that, F930S mutation causes the disappearance of the π bond between Phenylalanine at site 930 and Tyrosine at 836, K944N mutation changes the action direction of the side chain of Lysine at 944 with a regulatory subunit, V955G, V955I and V952A change spatial occupations of hydrophobic groups at important sites, and K966E mutation turns its action with milieu into mutual repulsion, and all of these will cause the conformation of PIK3CA to change, thereby resulting in the functional changes of PIK3CA (FIG. 3).

2, Functional Analysis by In Vitro Experiments

Experimental Method

The mutations K994N, F930S, V955G, V955I, K966E, V952A, and L983* of PIK3CA gene are introduced into the full-length coding sequence of PIK3CA gene (GenBank: NM_006218) by a point mutation technique. The full-length coding sequence of PIK3CA gene introduced with K994N mutation is the sequence obtained by mutating A at Position 2989 of the sequence having a GenBank accession number of NM_006218 into T; the full-length coding sequence of PIK3CA gene introduced with F930S mutation is the sequence obtained by mutating T at Position 2946 of the sequence having a GenBank accession number of NM_006218 into C; the full-length coding sequence of PIK3CA gene introduced with V955G mutation is the sequence obtained by mutating T at Position 3021 of the sequence having a GenBank accession number of NM_006218 into G; the full-length coding sequence of PIK3CA gene introduced with V955I mutation is the sequence obtained by mutating G at Position 3020 of the sequence having a GenBank accession number of NM_006218 into A; the full-length coding sequence of PIK3CA gene introduced with K966E mutation is the sequence obtained by mutating A at Position 3053 of the sequence having a GenBank accession number of NM_006218 into G; the full-length coding sequence of PIK3CA gene introduced with V952A mutation is the sequence obtained by mutating T at Position 3012 of the sequence having a GenBank accession number of NM_006218 into C; and the full-length coding sequence of PIK3CA gene introduced with L938* mutation is the sequence obtained by mutating T at Position 2970 of the sequence having a GenBank accession number of NM 006218 into A.

The above full-length coding sequence of wild-type PIK3CA gene (GenBank: NM_006218), and 7 mutant genes are linked to expression vectors (RC213112, Origene Company), respectively, and the vectors are transfected into colon cancer cell line DiFi after being verified by sequencing, wherein the transfection reagent is Lipofectamine™ 2000 (Lifetech, Inc., Cat. #11668-019).

Western blot assay and cell proliferation trial are performed on the DiFi cells over-expressing wild-type and mutant-type PIK3CA, in order to determine the changes of phosphorylation levels of AKT and ERK1/2 and the sensitivity of cells to cetuximab.

The specific steps of Western Blot assay are:

DiFi cells are cultured for 24 hours after being transfected with wild-type or mutant-type PIK3CA vectors, followed by cultured in serum free media for 12 hours, and then serum free media containing 100 nM cetuximab and/or 10 μM 5-FU are added for additional 24-hour culture. The above cultured cells are collected and dissolved with 1×RIPA buffer, and the protein concentrations are detected with BCA Protein Assay Kit (Thermo Scientific Cat. #23225). Equal amount of each sample is acquired for western blot assay, and the western blot assays are completed with the following antibodies: tag antibody (Sigma-aldrich, Cat. # F3165), p-AKT (Ser473) (Cell Signal, Cat. #4060), pan AKT (Cell Signal, Cat. #4685), p-ERK1/2 (Cell Signal, Cat. #4367), and total ERK1/2 (Cell Signal, Cat. #9107). At the same time, untransfected DiFi cells are set as negative control (Mock) in the experiment.

The specific steps of cell proliferation trial are:

DiFi cells are cultured for 24 hours after being transfected with wild-type or mutant-type PIK3CA vectors, and transferred to 96-well plate after being digested with trypsin and resuspended, with 3000 cells per well. Serum free media containing gradient concentrations of cetuximab (0.01 μg/ml to 10 μg/ml) is added or 10 μM fluorouracil (5-FU) is simultaneously added, and the cells are cultured until 48 hours after cell adherence. Thereafter, each well is added with 10 μl CCK-8, and co-cultured for 2 hours, the OD450 value is read on the machine, which is used for determining the cell survival rate (EnSpire™ 2300 Multilabel Reader, PerkinElmer).

The hotspot mutations E542K, E545K, and H1047R in Exons 9 and 20 of PIK3CA reported in the existing literatures are used as positive controls and also tested at the same time, and the specific experimental method is same as the above, wherein the full-length coding sequence of PIK3CA gene introduced with E542K mutation is the sequence obtained by replacing G at Position 1781 of the sequence having a GenBank accession number of NM_006218 with A; the full-length coding sequence of PIK3CA gene introduced with E545K mutation is the sequence obtained by replacing G at Position 1790 of the sequence having a GenBank accession number of NM_006218 with A; and the full-length coding sequence of PIK3CA gene introduced with H1047 mutation is the sequence obtained by replacing A at Position 3297 of the sequence having a GenBank accession number of NM_006218 with G.

The primer sequences for introducing the above mutation sites are specifically shown in Table 2.

TABLE 2

Primer Sequences for Introducing PIK3CA Gene Mutation Sites

| PIK3CA Mutation Sites | Primer Sequences |
|---|---|
| h PIK3CA F930S 5' | 5'-acgatggaca actgtctcat atagattttg gac-3' SEQ ID NO: 84 |
| h PIK3CA F930S 3' | 5'-atgagacagt tgtccatcgt ctttcaccat gat-3' SEQ ID NO: 85 |
| h PIK3CA K944N 5' | 5'-ggatcacaag aaaaaaatt ttggttataa ac-3' SEQ ID NO: 86 |
| h PIK3CA K944N 3' | 5'-aatttttctt cttgtgatcc aaaaagtgtc ca-3' SEQ ID NO: 87 |
| h PIK3CA V955G 5' | 5'-gtgccatttg gtttgacaca ggatttctta ata-3' SEQ ID NO: 88 |
| h PIK3CA V955G 3' | 5'-tgtgtcaaac caaatggcac acgttctcgt tta-3' SEQ ID NO: 89 |
| h PIK3CA V955I 5' | 5'-gtgccattta ttttgacaca ggatttctta ata-3' SEQ ID NO: 90 |
| h PIK3CA V955I 3' | 5'-tgtgtcaaaa taaatggcac acgttctcgt tta-3' SEQ ID NO: 91 |
| h PIK3CA K966E 5' | 5'-atagtgatta gtgaaggagc ccaagaatgc ac-3' SEQ ID NO: 92 |
| h PIK3CA K966E 3' | 5'-gctccttcac taatcactat taagaaatcc tg-3' SEQ ID NO: 93 |
| h PIK3CA L938* 5' | 5'-gacacttta ggatcacaag aagaaaaaat ttg-3' SEQ ID NO: 94 |
| h PIK3CA L938* 3' | 5'-cttgtgatcc taaaagtgtc caaatctat atg-3' SEQ ID NO: 95 |
| h PIK3CA V952A 5' | 5'-gcgccatttg ttttgacaca ggatttctta ata-3' SEQ ID NO: 96 |
| h PIK3CA V952A 3' | 5'-tgtgtcaaaa caaatggcgc acgttctcgt tta-3' SEQ ID NO: 97 |
| h PIK3CA E542K 5' | 5'-aaaatcactg agcaggagaa agattttcta tg-3' SEQ ID NO: 98 |
| h PIK3CA E542K 3' | 5'-ttctcctgct cagtgatttt agagagaggga tc-3' SEQ ID NO: 99 |
| h PIK3CA E545K 5' | 5'-gaaatcacta agcaggagaa agattttcta tg-3' SEQ ID NO: 100 |

TABLE 2 -continued

Primer Sequences for Introducing PIK3CA Gene Mutation Sites

| PIK3CA Mutation Sites | Primer Sequences |
|---|---|
| h PIK3CA E545K 3' | 5'-ttctcctgct tagtgatttc agagagaggga tc-3'<br>SEQ ID NO: 101 |
| h PIK3CA H1047R 5' | 5'-caaatgaatg atgcacgtca tggtggctgg ac-3'<br>SEQ ID NO: 102 |
| h PIK3CA H1047R 3' | 5'-tgacgtgcat cattcatttg tttcatgaaa tac-3'<br>SEQ ID NO: 103 |

Note:
the underlined bold-type letters represent the mutated codons (2) Results

The colon cancer cell line DiFi cells over-express wild-type PIK3CA and mutant-type PIK3CA (F930S, K944N, V955G, V955I, K966E, L938*, and V952A), at the same time, the hotspot mutations E542K, E545K, and H1047R reported in literatures are also tested.

Figure 4:
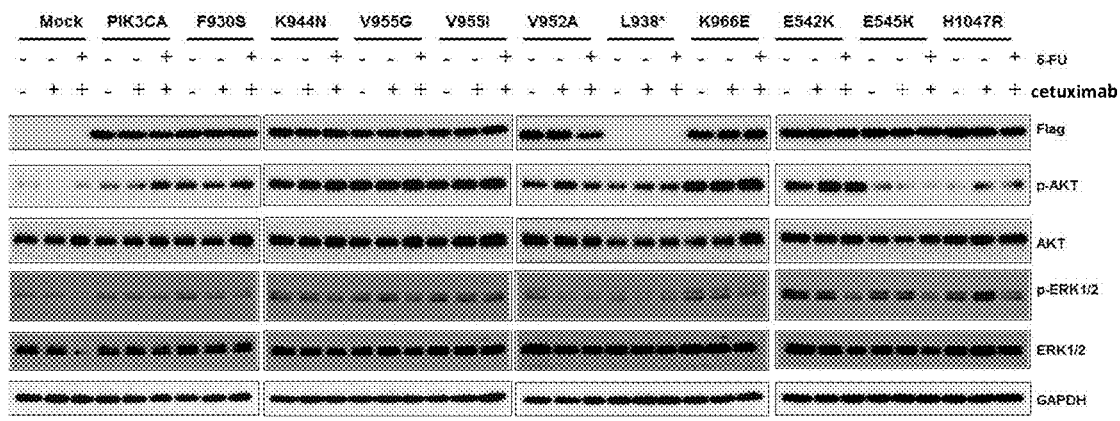
FIG. 4 is the effects of PIK3CA mutants on the phosphorylated expressions of downstream signals AKT and ERK1/2. The treated drugs are fluorouracil (5-FU) and cetuximab, respectively, and + represents treated; − represents untreated.

The results of Western blot show (FIG. 4):

In comparison with negatively transfected cells (Mock), after introduction of wild-type PIK3CA and mutant-type PIK3CA (F930S, K944N, V955G, V955I, K966E, L938*, V952A, and E542K) cells, the AKT phosphorylated expressions are obviously increased, while the AKT phosphorylated expressions of E545K and H1047R mutant-type cells are only slightly increased. Meanwhile, in K944N, V955G, V955I, K966E, E542K, E545K, and H1047R mutant-type cells, the phosphorylated expressions of ERK1/2 are also obviously increased.

After the cells are treated with 100 nM cetuximab, the AKT phosphorylations of negatively transfected cells are inhibited, but the AKT phosphorylations of the cells introduced with wild-type and mutant-type PIK3CA are not inhibited. The ERK1/2 phosphorylated expressions of negatively transfected cells are not affected, the ERK1/2 phosphorylated expressions of wild-type PIK3CA and mutant-type PIK3CA (K944N, V955G, V955I, K966E, and E545K) cells are not affected, the ERK1/2 phosphorylated expressions of H1047R cells are increased to some extent, and the ERK1/2 phosphorylated expressions of F930S, V952A, and E542K mutant-type cells are slightly decreased.

After the cells are treated with the combination of 100 nM cetuximab and 10 µM fluorouracil, the ERK1/2 phosphorylated expressions of negatively transfected cells are obviously decreased. In comparison with single administration of cetuximab, the ERK1/2 phosphorylated expressions of wild-type and all mutant-types PIK3CA are slightly decreased, but still higher than those of negatively transfected cells. The AKT phosphorylations of negatively transfected cells, wild-type and mutant-type PIK3CA cells are not inhibited.

Figure 5:
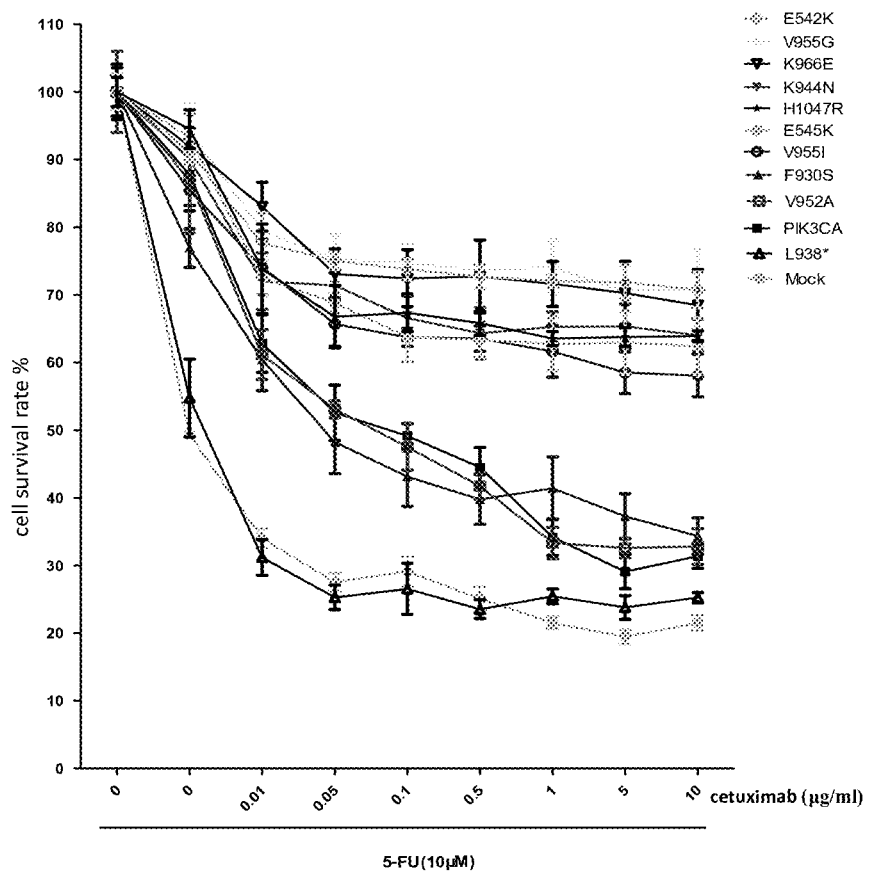
FIG. 5 is the effects of PIK3CA mutants on drug susceptibility. Mock is negative transfected cell, and E542K, E545K, H1047R are hotspot mutations detected in the tumor tissues which have been reported in literatures. L938* and V952A are mutations detected in the tumor tissues by the present study. The AKT phosphorylated expressions of F930S, K944N, V955G, V955I, and K966E mutant cells are obviously increased, and are not affected by cetuximab or cetuximab in combination with SFU; the ERK1/2 phosphorylated expressions are not affected under the action of cetuximab, and the ERK1/2 phosphorylated expressions are slightly decreased under the combined action of two drugs, but are still higher than those of negative transfected cells.

In cell proliferation trial, after addition of gradient concentrations of cetuximab and fixed 10 µM concentration of fluorouracil in serum-free media, all of the cells over-expressing K944N, V955G, V955I, K966E, E542K, E545K, and H1047R develop obvious drug resistances, the cells carrying wild-type PIK3CA, F930S, and V952A present moderate drug resistance, and L938* is same as negatively transfected cells (Mock), which is sensitive to drug effects (FIG. 5).

The results of the above in vitro experiments demonstrate that the new mutations F930S, K944N, V955G, V955I, and K966E of PIK3CA found in ctDNA have the functions of activating downstream molecules and causing the drug resistance of cetuximab.

Example 2, the Actual Uses of PIK3CA Gene Mutations which are Important Factors Resulting in the Drug Resistance of Cetuximab in the Treatment of Metastatic Colorectal Cancer I, Determination of the Method for Detecting the Drug Resistance of Cetuximab in the Treatment of Metastatic Colorectal Cancer Based on the study results of Example 1, the method for detecting the drug resistance of cetuximab in the treatment of metastatic colorectal cancer is established. Details are as follows:

A patient with metastatic colorectal cancer, who is intended to receive cetuximab treatment or is receiving cetuximab treatment and does not develop drug resistance, is used as a subject to be tested, and the PIK3CA gene of the subject to be tested is subjected to point mutation analysis.

if the Exon 19 in PIK3CA gene of the patient with metastatic colorectal cancer as the subject to be tested, who is intended to receive cetuximab treatment or is receiving cetuximab treatment and does not develop drug resistance, has at least one of following (a)-(e) mutations, the subject to be tested will develop drug resistance or will be a candidate that develops drug resistance when receiving or continuing to receive cetuximab for treating metastatic colorectal cancer:

(a) Lysine at the 944th amino acid of the PIK3CA gene coding protein mutates into Asparagine (K944N);
(b) Phenylalanine at 930th amino acid of the PIK3CA gene coding protein mutates into Serine (F930S);
(c) Valine at the 955th amino acid of the PIK3CA gene coding protein mutates into Isoleucine (V955I);
(d) Valine at the 955th amino acid of the PIK3CA gene coding protein mutates into Glycine (V955G); and
(e) Lysine at the 966th amino acid of the PIK3CA gene coding protein mutates into Glutamic Acid (K966E).

Each mutation corresponds to gene level, and is specifically embodied as:
the (a) is A at Position 48 in the Exon 19 of the PIK3CA gene mutates into T;
the (b) is Tat Position 5 in the Exon 19 of the PIK3CA gene mutates into C;
the (c) is G at Position 79 in the Exon 19 of the PIK3CA gene mutates into A;
the (d) is T at Position 80 in the Exon 19 of the PIK3CA gene mutates into G; and the (e) is A at Position 112 in the Exon 19 of the PIK3CA gene mutates into G.

Where, the nucleotide sequence of the Exon 19 in the PIK3CA gene (wild-type) is shown as SEQ ID NO: 1 in the Sequence List.

II, Actual Uses of the Method for Detecting the Drug Resistance of Cetuximab in the Treatment of Metastatic Colorectal Cancer 1, Patient Samples to be Tested There are a total of 44 patients with metastatic colorectal cancer who are intended to receive cetuximab treatment or are receiving cetuximab treatment and do not develop drug resistance. All of the patients signed informed consents.

2, Detection and Clinic Verification of Gene Mutations in Circulating Tumor DNA (ctDNA) of the Patients to be Tested In one aspect, a series of plasma samples of the patients to be tested before treatment, during treatment, and after occurrence of drug resistance are collected, once every four weeks, to analyze the dynamic changes of tumor-related gene mutations in ctDNA.

Exon 19 of PIK3CA gene (wild-type gene as shown in SEQ ID NO: 1) and other genes (for example, BRAF, AKT1, EGFR, PTEN and other genes) are sequenced using the method recorded in Example 1, and it is judged whether the patients to be tested will develop drug resistance when continuing to treat metastatic colorectal cancer with cetuximab, according to the method recorded in Step I.

Where, the primers employed in sequencing are specifically shown in Table 1 of Example 1.

In another aspect, all patients to be tested are subjected to drug resistance verification by clinically conventional imageology detection means, and these patients receive cetuximab treatment, and are examined every 6 weeks by CT, the therapeutic effects are evaluated with RECIST 1.1, and it is judged to have drug resistance if the evaluation is disease progression (progression free survival (PFS)≥6 weeks, secondary drug resistance; and PFS<6 weeks, primary drug resistance).

The results of clinically conventional imageology detection means show that, 12 of 44 patients to be tested have primary drug resistance, and 32 cases have secondary drug resistance. In all of 32 secondary resistant patients to be tested, gene mutations are detected in a total of 18 cases, wherein mutations (F930S, K944N, V955G, V955I or K966E) in Exon 19 of PIK3CA gene are detected for 7 cases, mutations of KRAS gene are detected for 8 cases, and other mutations are distributed in BRAF, AKT1, EGFR, and PTEN genes. It can be seen that PIK3CA gene employed in the present invention is the important reason resulting in the drug resistance of cetuximab, only second to KRAS gene mutations. In 12 primary resistant patients, the above 5 kinds of mutations in Exon 19 of PIK3CA gene are detected in the plasma of 5 patents before treatment, suggesting that the mutations in Exon 19 of PIK3CA gene have important role in both primary drug resistance and secondary drug resistance. The results and time points to positive of clinically conventional imageology detection and gene mutation detection for secondary resistant patients and primary resistant patients are specifically shown in Table 3 and Table 4. It can be seen that the occurrence of PIK3CA gene mutation is earlier than the drug resistance time evaluated by imageology, which is significance in instruction of the clinical medications for metastatic colorectal cancer patients.

TABLE 3 gene mutations and detections of drug resistance in secondary resistant patients

| Patient Number | Genome Information | Transcripts | Genes | Exons | Amino Acid Mutation Sites | Times to Positive of Mutation Sites (days after treatment) | Times to Positive of Drug Resistance by Imageology Evaluation |
|---|---|---|---|---|---|---|---|
| 2 | chr12_25380275_T_G | NM_004985 | KRAS | 3 | Q61H | Day 54 | Day 157 |
| 6 | chr3_178948060_A_T | NM_006218 | PIK3CA | 19 | K944N | Day 139 | Day 286 |
| 7 | chr3_178948091_G_A | NM_006218 | PIK3CA | 19 | V955I | Day 279 | Day 319 |
| 12 | chr7_55227909_G_A | NM_005228 | EGFR | 12 | G459E | Day 210 | Day 238 |
|  | chr12_25398284_C_T | NM_004985 | KRAS | 2 | G12D | Day 120 | Day 238 |
|  | chr12_25398281_C_T | NM_004985 | KRAS | 2 | G13D | Day 197 | Day 238 |
| 13 | chr12_25398284_C_T | NM_004985 | KRAS | 2 | G12D | Day 216 | no progression until Day 284 |
|  | chr12_25398281_C_T | NM_004985 | KRAS | 2 | G13D | Day 216 | Day 284 |
| 14 | chr7_140453136_A_T | NM_004333 | BRAF | 15 | V600E | Day 322 | Day 322 |
| 16 | chr3_178948060_A_T | NM_006218 | PIK3CA | 19 | K944N | Day 119 | Day 147 |
| 17 | chr3_178948060_A_T | NM_006218 | PIK3CA | 19 | K944N | Day 49 | Day 155 |
| 19 | chr12_25398284_C_T | NM_004985 | KRAS | 2 | G12D | Day 364 | Day 392 |
|  | chr12_25398281_C_T | NM_004985 | KRAS | 2 | G13D | Day 364 | Day 392 |
| 20 | chr10_89717708_C_T | NM_000314 | PTEN | 7 | Q245* | Day 99 | no progression until Day 143 |
| 21 | chr12_25378686_C_A | NM_004985 | KRAS | 4 | K104N | — | — |
|  | chr3_178948017_T_C | NM_006218 | PIK3CA | 19 | F930S | — | — |
| 22 | chr3_178948092_T_G | NM_006218 | PIK3CA | 19 | V955G | — | — |
|  | chr14_105246536_A_C | NM_001014431 | AKT1 | 3 | W22G | — | — |
| 23 | chr7_140453076_A_T | NM_004333 | BRAF | 15 | M620K | — | — |
|  | chr12_25398233_A_G | NM_004985 | KRAS | 2 | V29A | — | — |
| 27 | chr17_7578255_T_A | NM_000546 | TP53 | 5 | E198D | — | — |
|  | chr3_178948124_A_G | NM_006218 | PIK3CA | 19 | K966E | — | — |
| 28 | chr12_25398304_T_G | NM_004985 | KRAS | 2 | K5N | — | — |
| 29 | chr10_89692916_A_T | NM_000314 | PTEN | 5 | M134L | — | — |

TABLE 3-continued gene mutations and detections of drug resistance in secondary resistant patients

| | Gene Mutation Detection | | | | | | |
|---|---|---|---|---|---|---|---|
| Patient Number | Genome Information | Transcripts | Genes | Exons | Amino Acid Mutation Sites | Times to Positive of Mutation Sites (days after treatment) | Times to Positive of Drug Resistance by Imageology Evaluation |
| 33 | chr7_140453181_T_C | NM_004333 | BRAF | 15 | H585R | — | — |
| 34 | chr12_25398284_C_A | NM_004985 | KRAS | 2 | G12V | — | — |

Note:
plasma samples at a series of time points are not collected from No. 21 to No. 34 patients, thus PIK3CA gene mutation detections and drug resistance times evaluated by imageology cannot be compared.

TABLE 4

PIK3CA gene mutations and detections of drug resistance in primary resistant patients

| | | PIK3CA mutation detection | | Times to Positive of Drug Resistance by Imageology |
|---|---|---|---|---|
| Patient Number | Genome Information | PIK3CA Mutations | Times to Positive of Mutation Sites | Evaluation (days from the beginning of the treatment) |
| 41 | chr3_178948017_T_C | F930S | before treatment | 42 |
| | chr3_178948124_A_G | K966E | before treatment | 42 |
| 44 | chr3_178948017_T_C | F930S | before treatment | 28 |
| 46 | chr3_178948060_A_T | K944N | before treatment | 28 |
| | chr3_178948124_A_G | K966E | before treatment | 28 |
| 47 | chr3_178948092_T_G | V955G | before treatment | 42 |
| 49 | chr3_178948060_A_T | K944N | before treatment | 42 |
| | chr3_178948091_G_A | V955I | before treatment | 42 |

In consideration of the above study results of Examples in the present invention, the present invention discoveries mutations (F930S, K944N, V955G, V955I, and K966E) in Exon 19 of PIK3CA gene which have an importance nearly same as the KRAS gene mutations in circulating tumor DNA (ctDNA) reported in the research report in Nature that was issued by Diaz Jr et al. in 2012, thus the present invention further improve the reasons for drug resistances of EGFR monoclonal antibodies.

INDUSTRIAL APPLICATIONS

The present invention analyzes the mutations of plasma ctDNA before treatment or during treatment by means of deep sequencing technique, and wish to have a more comprehensive understanding of mutations that are related to the drug resistance of cetuximab. 5 kinds of point mutations in Exon 19 of PIK3CA gene which are significantly related to the drug resistance of cetuximab are finally confirmed in ctDNA, and are K944N, F930S, V955I, V955G, and K966E, respectively. In a total of 32 secondary resistant patients, 7 (21.9%) patients have PIK3CA mutations, 8 (25%) patients have KRAS mutations, and in the plasma of 12 primary resistant patients before treatment, 5 cases have PIK3CA mutations. Therefore, the contribution of PIK3CA gene mutation to the drug resistance of cetuximab is similar with that of KRAS gene. The in vitro experiments demonstrate that, in comparison with wild-type PIK3CA, PIK3CA mutants can significantly promote the phosphorylation of downstream signal AKT, and can result in the drug resistance of colon cancer cells DiFi to cetuximab. The present invention verifies that PIK3CA gene mutations are important factors that cause the drug resistance of cetuximab; in the studies of gene mutations relating to drug resistance, deep sequencing of the amplicons of target genes based on a series of plasma samples before treatment and during treatment is a feasible and effective method. Moreover, the occurrence of PIK3CA gene mutation is earlier than the drug resistance time evaluated by imageology, which is significance in instruction of the clinical medications for metastatic colorectal cancer patients.

The invention claimed is:

1. A method for diagnosing or assisting in diagnosing of acquired cetuximab resistance in metastatic colorectal cancer in a subject, the method comprising administering a substance used for detecting whether Exon 19 in the PIK3CA gene of the subject has a gene mutation, wherein the substance used for detecting whether Exon 19 in the PIK3CA gene has a gene mutation is Primer Pair 1 and/or Primer Pair 2, wherein Primer Pair 1 is a primer pair composed of two single stranded DNA molecules shown by SEQ ID NO: 2 and SEQ ID NO: 3, and wherein Primer Pair 2 is a primer pair composed of two single stranded DNA molecules shown by SEQ ID NO: 4 and SEQ ID NO: 5;
    detecting whether the subject has at least one of following (a)-(e) mutations:
      (a) Lysine at the 944th amino acid of the PIK3CA gene coding protein mutates into Asparagine;
      (b) Phenylalanine at the 930th amino acid of the PIK3CA gene coding protein mutates into Serine;
      (c) Valine at the 955th amino acid of the PIK3CA gene coding protein mutates into Isoleucine;
      (d) Valine at the 955th amino acid of the PIK3CA gene coding protein mutates into Glycine; and
      (e) Lysine at the 966th amino acid of the PIK3CA gene coding protein mutates into Glutamic Acid; and
    determining that the subject will develop drug resistance or will be a candidate that develops drug resistance when receiving or continuing to receive cetuximab for treating metastatic colorectal cancer, if the subject has at least one of the above (a)-(e) mutations.

2. The method according to claim 1, wherein the gene mutation in Exon 19 of the PIK3CA gene is at least one of:
    (a) A at Position 48 of a nucleotide sequence of Exon 19 of the PIK3CA gene mutates into T;
    (b) T at position 5 of the nucleotide sequence of Exon 19 of the PIK3CA gene mutates into C;
    (c) G at position 79 of the nucleotide sequence of Exon 19 of the PIK3CA gene mutates into A;
    (d) T at position 80 of the nucleotide sequence of Exon 19 of the PIK3CA gene mutates into G; and
    (e) A at position 112 of the nucleotide sequence of Exon 19 of the PIK3CA gene mutates into G.

* * * * *

SEQUENCE LISTING

```
<160> NUMBER OF SEQ ID NOS: 103

<210> SEQ ID NO 1
<211> LENGTH: 152
<212> TYPE: DNA
<213> ORGANISM: Homo sapiens
<220> FEATURE:
<223> OTHER INFORMATION:
```

-continued

<400> SEQUENCE: 1
ctgtttcata tagattttgg acacttttg gatcacaaga agaaaaaatt tggttataaa    60
cgagaacgtg tgccatttgt tttgacacag gatttcttaa tagtgattag taaaggagcc  120
caagaatgca caaagacaag agaatttgag ag                                152

<210> SEQ ID NO 2
<211> LENGTH: 33
<212> TYPE: DNA
<213> ORGANISM: Artificial Sequence
<220> FEATURE:
<223> OTHER INFORMATION: Other Information: Primer

<400> SEQUENCE: 2
attcaagaca ttttgtatct gcatatatca aac                                 33

<210> SEQ ID NO 3
<211> LENGTH: 27
<212> TYPE: DNA
<213> ORGANISM: Artificial Sequence
<220> FEATURE:
<223> OTHER INFORMATION: Other Information: Primer

<400> SEQUENCE: 3
gcacacgttc tcgtttataa ccaaatt                                        27

<210> SEQ ID NO 4
<211> LENGTH: 28
<212> TYPE: DNA
<213> ORGANISM: Artificial Sequence
<220> FEATURE:
<223> OTHER INFORMATION: Other Information: Primer

<400> SEQUENCE: 4
gattttggac acttttgga tcacaaga                                        28

<210> SEQ ID NO 5
<211> LENGTH: 24
<212> TYPE: DNA
<213> ORGANISM: Artificial Sequence
<220> FEATURE:
<223> OTHER INFORMATION: Other Information: Primer

<400> SEQUENCE: 5 gtgttttaa ttgctcgagc tcac                                            24

<210> SEQ ID NO 6
<211> LENGTH: 21
<212> TYPE: DNA
<213> ORGANISM: Artificial Sequence
<220> FEATURE:
<223> OTHER INFORMATION: Other Information: Primer

<400> SEQUENCE: 6
cccccaaatc tgaatcccga g                                              21

<210> SEQ ID NO 7
<211> LENGTH: 23
<212> TYPE: DNA
<213> ORGANISM: Artificial Sequence
<220> FEATURE:
<223> OTHER INFORMATION: Other Information: Primer

<400> SEQUENCE: 7
ctcctcaaga atgatggcac ctt                                           23

<210> SEQ ID NO 8
<211> LENGTH: 19
<212> TYPE: DNA
<213> ORGANISM: Artificial Sequence
<220> FEATURE:
<223> OTHER INFORMATION: Other Information: Primer

<400> SEQUENCE: 8
gccgctcctt gtagccaat                                                19

<210> SEQ ID NO 9
<211> LENGTH: 20
<212> TYPE: DNA
<213> ORGANISM: Artificial Sequence
<220> FEATURE:
<223> OTHER INFORMATION: Other Information: Primer

<400> SEQUENCE: 9
gggtctgacg ggtagagtgt                                               20

<210> SEQ ID NO 10
<211> LENGTH: 25
<212> TYPE: DNA
<213> ORGANISM: Artificial Sequence
<220> FEATURE:
<223> OTHER INFORMATION: Other Information: Primer

<400> SEQUENCE: 10
catccacaaa atggatccag acaac                                         25

<210> SEQ ID NO 11
<211> LENGTH: 25
<212> TYPE: DNA
<213> ORGANISM: Artificial Sequence
<220> FEATURE:
<223> OTHER INFORMATION: Other Information: Primer

<400> SEQUENCE: 11
gcttgctctg ataggaaaat gagat                                         25

<210> SEQ ID NO 12
<211> LENGTH: 28
<212> TYPE: DNA
<213> ORGANISM: Artificial Sequence
<220> FEATURE:
<223> OTHER INFORMATION: Other Information: Primer

<400> SEQUENCE: 12
gttgagacct tcaatgactt tctagtaa                                      28

<210> SEQ ID NO 13
<211> LENGTH: 22
<212> TYPE: DNA
<213> ORGANISM: Artificial Sequence
<220> FEATURE:
<223> OTHER INFORMATION: Other Information: Primer

<400> SEQUENCE: 13
gtgggtccca tcagtttgaa ca                                            22

<210> SEQ ID NO 14
<211> LENGTH: 20
<212> TYPE: DNA
<213> ORGANISM: Artificial Sequence

```
<220> FEATURE:
<223> OTHER INFORMATION: Other Information: Primer

<400> SEQUENCE: 14
acctccatca gtggcgatct                                               20

<210> SEQ ID NO 15
<211> LENGTH: 24
<212> TYPE: DNA
<213> ORGANISM: Artificial Sequence
<220> FEATURE:
<223> OTHER INFORMATION: Other Information: Primer

<400> SEQUENCE: 15
cagaggagga gtatgtgtga agga                                          24

<210> SEQ ID NO 16
<211> LENGTH: 24
<212> TYPE: DNA
<213> ORGANISM: Artificial Sequence
<220> FEATURE:
<223> OTHER INFORMATION: Other Information: Primer

<400> SEQUENCE: 16
caccctgttg tttgtttcag tgac                                          24

<210> SEQ ID NO 17
<211> LENGTH: 27
<212> TYPE: DNA
<213> ORGANISM: Artificial Sequence
<220> FEATURE:
<223> OTHER INFORMATION: Other Information: Primer

<400> SEQUENCE: 17
aacaggaaat atgtcgaaaa gttctct                                       27

<210> SEQ ID NO 18
<211> LENGTH: 24
<212> TYPE: DNA
<213> ORGANISM: Artificial Sequence
<220> FEATURE:
<223> OTHER INFORMATION: Other Information: Primer

<400> SEQUENCE: 18
gtcaatcaaa ggtggtctgg agaa                                          24

<210> SEQ ID NO 19
<211> LENGTH: 20
<212> TYPE: DNA
<213> ORGANISM: Artificial Sequence
<220> FEATURE:
<223> OTHER INFORMATION: Other Information: Primer

<400> SEQUENCE: 19
agggagcgta atcccaagga                                               20

<210> SEQ ID NO 20
<211> LENGTH: 28
<212> TYPE: DNA
<213> ORGANISM: Artificial Sequence
<220> FEATURE:
<223> OTHER INFORMATION: Other Information: Primer

<400> SEQUENCE: 20
gtgctatgca aatacaataa actggaaa                                      28
```

<210> SEQ ID NO 21
<211> LENGTH: 29
<212> TYPE: DNA
<213> ORGANISM: Artificial Sequence
<220> FEATURE:
<223> OTHER INFORMATION: Other Information: Primer

<400> SEQUENCE: 21
acaaataaag gacccattag aaccaactc                               29

<210> SEQ ID NO 22
<211> LENGTH: 23
<212> TYPE: DNA
<213> ORGANISM: Artificial Sequence
<220> FEATURE:
<223> OTHER INFORMATION: Other Information: Primer

<400> SEQUENCE: 22
cagtcgtcag cctgaacata aca                                     23

<210> SEQ ID NO 23
<211> LENGTH: 19
<212> TYPE: DNA
<213> ORGANISM: Artificial Sequence
<220> FEATURE:
<223> OTHER INFORMATION: Other Information: Primer

<400> SEQUENCE: 23
ctgaccggag gtcccaaac                                          19

<210> SEQ ID NO 24
<211> LENGTH: 21
<212> TYPE: DNA
<213> ORGANISM: Artificial Sequence
<220> FEATURE:
<223> OTHER INFORMATION: Other Information: Primer

<400> SEQUENCE: 24
ccagctccaa ctaccacaag t                                       21

<210> SEQ ID NO 25
<211> LENGTH: 31
<212> TYPE: DNA
<213> ORGANISM: Artificial Sequence
<220> FEATURE:
<223> OTHER INFORMATION: Other Information: Primer

<400> SEQUENCE: 25
ctggtggagt atttgatagt gtattaacct t                            31

<210> SEQ ID NO 26
<211> LENGTH: 23
<212> TYPE: DNA
<213> ORGANISM: Artificial Sequence
<220> FEATURE:
<223> OTHER INFORMATION: Other Information: Primer

<400> SEQUENCE: 26
aaagaatggt cctgcaccag taa                                     23

<210> SEQ ID NO 27
<211> LENGTH: 27
<212> TYPE: DNA
<213> ORGANISM: Artificial Sequence
<220> FEATURE:
<223> OTHER INFORMATION: Other Information: Primer

```
<400> SEQUENCE: 27
aggcctgctg aaaatgactg aatataa                                      27

<210> SEQ ID NO 28
<211> LENGTH: 18
<212> TYPE: DNA
<213> ORGANISM: Artificial Sequence
<220> FEATURE:
<223> OTHER INFORMATION: Other Information: Primer

<400> SEQUENCE: 28
gaaagccctc cccagtcc                                                18

<210> SEQ ID NO 29
<211> LENGTH: 27
<212> TYPE: DNA
<213> ORGANISM: Artificial Sequence
<220> FEATURE:
<223> OTHER INFORMATION: Other Information: Primer

<400> SEQUENCE: 29
tgcactgtaa taatccagac tgtgttt                                      27

<210> SEQ ID NO 30
<211> LENGTH: 33
<212> TYPE: DNA
<213> ORGANISM: Artificial Sequence
<220> FEATURE:
<223> OTHER INFORMATION: Other Information: Primer

<400> SEQUENCE: 30
aatgtcagct tattatattc aatttaaacc cac                               33

<210> SEQ ID NO 31
<211> LENGTH: 22
<212> TYPE: DNA
<213> ORGANISM: Artificial Sequence
<220> FEATURE:
<223> OTHER INFORMATION: Other Information: Primer

<400> SEQUENCE: 31
gcaatgaggg accagtacat ga                                           22

<210> SEQ ID NO 32
<211> LENGTH: 27
<212> TYPE: DNA
<213> ORGANISM: Artificial Sequence
<220> FEATURE:
<223> OTHER INFORMATION: Other Information: Primer

<400> SEQUENCE: 32
actgttctag aaggcaaatc acattta                                      27

<210> SEQ ID NO 33
<211> LENGTH: 28
<212> TYPE: DNA
<213> ORGANISM: Artificial Sequence
<220> FEATURE:
<223> OTHER INFORMATION: Other Information: Primer

<400> SEQUENCE: 33
gtggacaggt tttgaaagat atttgtgt                                     28

<210> SEQ ID NO 34
```

```
<211> LENGTH: 31
<212> TYPE: DNA
<213> ORGANISM: Artificial Sequence
<220> FEATURE:
<223> OTHER INFORMATION: Other Information: Primer

<400> SEQUENCE: 34
aatgacataa cagttatgat tttgcagaaa a                              31

<210> SEQ ID NO 35
<211> LENGTH: 23
<212> TYPE: DNA
<213> ORGANISM: Artificial Sequence
<220> FEATURE:
<223> OTHER INFORMATION: Other Information: Primer

<400> SEQUENCE: 35
caggctcagg acttagcaag aag                                      23

<210> SEQ ID NO 36
<211> LENGTH: 31
<212> TYPE: DNA
<213> ORGANISM: Artificial Sequence
<220> FEATURE:
<223> OTHER INFORMATION: Other Information: Primer

<400> SEQUENCE: 36
ctttgctgat gtttcaataa aaggaattcc a                             31

<210> SEQ ID NO 37
<211> LENGTH: 27
<212> TYPE: DNA
<213> ORGANISM: Artificial Sequence
<220> FEATURE:
<223> OTHER INFORMATION: Other Information: Primer

<400> SEQUENCE: 37
gactctgaag atgtacctat ggtccta                                  27

<210> SEQ ID NO 38
<211> LENGTH: 26
<212> TYPE: DNA
<213> ORGANISM: Artificial Sequence
<220> FEATURE:
<223> OTHER INFORMATION: Other Information: Primer

<400> SEQUENCE: 38
tcacctctat ggtgggatca tattca                                   26

<210> SEQ ID NO 39
<211> LENGTH: 24
<212> TYPE: DNA
<213> ORGANISM: Artificial Sequence
<220> FEATURE:
<223> OTHER INFORMATION: Other Information: Primer

<400> SEQUENCE: 39
accctgatta ctggtttcca acag                                     24

<210> SEQ ID NO 40
<211> LENGTH: 33
<212> TYPE: DNA
<213> ORGANISM: Artificial Sequence
<220> FEATURE:
<223> OTHER INFORMATION: Other Information: Primer

<400> SEQUENCE: 40
```
aaataacttt ttactttctc tcctcttatt cct        33

<210> SEQ ID NO 41
<211> LENGTH: 26
<212> TYPE: DNA
<213> ORGANISM: Artificial Sequence
<220> FEATURE:
<223> OTHER INFORMATION: Other Information: Primer

<400> SEQUENCE: 41
cagctaatcc agaaccactt tgtaga        26

<210> SEQ ID NO 42
<211> LENGTH: 27
<212> TYPE: DNA
<213> ORGANISM: Artificial Sequence
<220> FEATURE:
<223> OTHER INFORMATION: Other Information: Primer

<400> SEQUENCE: 42
aaaagctcta tcttccctag tgtggta        27

<210> SEQ ID NO 43
<211> LENGTH: 28
<212> TYPE: DNA
<213> ORGANISM: Artificial Sequence
<220> FEATURE:
<223> OTHER INFORMATION: Other Information: Primer

<400> SEQUENCE: 43
gcttcctctg tgtatttgcc atcaataa        28

<210> SEQ ID NO 44
<211> LENGTH: 26
<212> TYPE: DNA
<213> ORGANISM: Artificial Sequence
<220> FEATURE:
<223> OTHER INFORMATION: Other Information: Primer

<400> SEQUENCE: 44
tcttcttgtc cagctgtatc cagtat        26

<210> SEQ ID NO 45
<211> LENGTH: 23
<212> TYPE: DNA
<213> ORGANISM: Artificial Sequence
<220> FEATURE:
<223> OTHER INFORMATION: Other Information: Primer

<400> SEQUENCE: 45
aaaaattgaa cttccctccc tcc        23

<210> SEQ ID NO 46
<211> LENGTH: 27
<212> TYPE: DNA
<213> ORGANISM: Artificial Sequence
<220> FEATURE:
<223> OTHER INFORMATION: Other Information: Primer

<400> SEQUENCE: 46
aggttaatat ccgcaaatga cttgcta        27

<210> SEQ ID NO 47
<211> LENGTH: 24
<212> TYPE: DNA

<210> SEQ ID NO 47
<211> LENGTH: 24
<212> TYPE: DNA
<213> ORGANISM: Artificial Sequence
<220> FEATURE:
<223> OTHER INFORMATION: Other Information: Primer

<400> SEQUENCE: 47
gatggtgaaa cctgtttgtt ggac                                        24

<210> SEQ ID NO 48
<211> LENGTH: 28
<212> TYPE: DNA
<213> ORGANISM: Artificial Sequence
<220> FEATURE:
<223> OTHER INFORMATION: Other Information: Primer

<400> SEQUENCE: 48
gaatatggat cacatctcta ccagagtt                                    28

<210> SEQ ID NO 49
<211> LENGTH: 24
<212> TYPE: DNA
<213> ORGANISM: Artificial Sequence
<220> FEATURE:
<223> OTHER INFORMATION: Other Information: Primer

<400> SEQUENCE: 49
gccaagagtt acgggattcc attc                                        24

<210> SEQ ID NO 50
<211> LENGTH: 22
<212> TYPE: DNA
<213> ORGANISM: Artificial Sequence
<220> FEATURE:
<223> OTHER INFORMATION: Other Information: Primer

<400> SEQUENCE: 50
tggtcttggc tgaggtttca at                                          22

<210> SEQ ID NO 51
<211> LENGTH: 25
<212> TYPE: DNA
<213> ORGANISM: Artificial Sequence
<220> FEATURE:
<223> OTHER INFORMATION: Other Information: Primer

<400> SEQUENCE: 51
tcccgttttt agggagcaga ttaag                                       25

<210> SEQ ID NO 52
<211> LENGTH: 27
<212> TYPE: DNA
<213> ORGANISM: Artificial Sequence
<220> FEATURE:
<223> OTHER INFORMATION: Other Information: Primer

<400> SEQUENCE: 52
tttttatggc agtcaaacct tctctct                                     27

<210> SEQ ID NO 53
<211> LENGTH: 22
<212> TYPE: DNA
<213> ORGANISM: Artificial Sequence
<220> FEATURE:
<223> OTHER INFORMATION: Other Information: Primer

<400> SEQUENCE: 53
cagaccaatt ggcatgctct tc                                          22

<210> SEQ ID NO 54
<211> LENGTH: 28
<212> TYPE: DNA
<213> ORGANISM: Artificial Sequence
<220> FEATURE:
<223> OTHER INFORMATION: Other Information: Primer

<400> SEQUENCE: 54
ggtaaagttc ccagatatgt cagtgatt                                              28

<210> SEQ ID NO 55
<211> LENGTH: 33
<212> TYPE: DNA
<213> ORGANISM: Artificial Sequence
<220> FEATURE:
<223> OTHER INFORMATION: Other Information: Primer

<400> SEQUENCE: 55
aattgatact taataaactc agtgatttgc ctt                                         33

<210> SEQ ID NO 56
<211> LENGTH: 28
<212> TYPE: DNA
<213> ORGANISM: Artificial Sequence
<220> FEATURE:
<223> OTHER INFORMATION: Other Information: Primer

<400> SEQUENCE: 56
tgcaacattt ctaaagttac ctacttgt                                               28

<210> SEQ ID NO 57
<211> LENGTH: 26
<212> TYPE: DNA
<213> ORGANISM: Artificial Sequence
<220> FEATURE:
<223> OTHER INFORMATION: Other Information: Primer

<400> SEQUENCE: 57
tggtcaagat cttcacaaaa gggttt                                                 26

<210> SEQ ID NO 58
<211> LENGTH: 25
<212> TYPE: DNA
<213> ORGANISM: Artificial Sequence
<220> FEATURE:
<223> OTHER INFORMATION: Other Information: Primer

<400> SEQUENCE: 58
gaaagggacg aactggtgta atgat                                                  25

<210> SEQ ID NO 59
<211> LENGTH: 29
<212> TYPE: DNA
<213> ORGANISM: Artificial Sequence
<220> FEATURE:
<223> OTHER INFORMATION: Other Information: Primer

<400> SEQUENCE: 59
ataaattctc agatccagga agaggaaag                                              29

<210> SEQ ID NO 60
<211> LENGTH: 25
<212> TYPE: DNA
<213> ORGANISM: Artificial Sequence
<220> FEATURE:

<223> OTHER INFORMATION: Other Information: Primer

<400> SEQUENCE: 60
taacccacca cagctagaac ttatc 25

<210> SEQ ID NO 61
<211> LENGTH: 26
<212> TYPE: DNA
<213> ORGANISM: Artificial Sequence
<220> FEATURE:
<223> OTHER INFORMATION: Other Information: Primer

<400> SEQUENCE: 61
tgccccgatg taataaatat gcacat 26

<210> SEQ ID NO 62
<211> LENGTH: 23
<212> TYPE: DNA
<213> ORGANISM: Artificial Sequence
<220> FEATURE:
<223> OTHER INFORMATION: Other Information: Primer

<400> SEQUENCE: 62
cgacgggaag acaagttcat gta 23

<210> SEQ ID NO 63
<211> LENGTH: 29
<212> TYPE: DNA
<213> ORGANISM: Artificial Sequence
<220> FEATURE:
<223> OTHER INFORMATION: Other Information: Primer

<400> SEQUENCE: 63
tgtccttatt ttggatattt ctcccaatg 29

<210> SEQ ID NO 64
<211> LENGTH: 24
<212> TYPE: DNA
<213> ORGANISM: Artificial Sequence
<220> FEATURE:
<223> OTHER INFORMATION: Other Information: Primer

<400> SEQUENCE: 64
gacagttaaa ggcatttcct gtga 24

<210> SEQ ID NO 65
<211> LENGTH: 22
<212> TYPE: DNA
<213> ORGANISM: Artificial Sequence
<220> FEATURE:
<223> OTHER INFORMATION: Other Information: Primer

<400> SEQUENCE: 65
gtaacggctg agggaactca aa 22

<210> SEQ ID NO 66
<211> LENGTH: 31
<212> TYPE: DNA
<213> ORGANISM: Artificial Sequence
<220> FEATURE:
<223> OTHER INFORMATION: Other Information: Primer

<400> SEQUENCE: 66
tcacttttgg gtaaatacat tcttcatacc a 31

```
<210> SEQ ID NO 67
<211> LENGTH: 25
<212> TYPE: DNA
<213> ORGANISM: Artificial Sequence
<220> FEATURE:
<223> OTHER INFORMATION: Other Information: Primer

<400> SEQUENCE: 67
atattccttg tcattatctg cacgc                                           25

<210> SEQ ID NO 68
<211> LENGTH: 28
<212> TYPE: DNA
<213> ORGANISM: Artificial Sequence
<220> FEATURE:
<223> OTHER INFORMATION: Other Information: Primer

<400> SEQUENCE: 68
aagaaatcga tagcatttgc agtataga                                        28

<210> SEQ ID NO 69
<211> LENGTH: 24
<212> TYPE: DNA
<213> ORGANISM: Artificial Sequence
<220> FEATURE:
<223> OTHER INFORMATION: Other Information: Primer

<400> SEQUENCE: 69
tggagaaaag tatcggttgg cttt                                            24

<210> SEQ ID NO 70
<211> LENGTH: 29
<212> TYPE: DNA
<213> ORGANISM: Artificial Sequence
<220> FEATURE:
<223> OTHER INFORMATION: Other Information: Primer

<400> SEQUENCE: 70 ttgactttt gcaaatgttt aacataggt                                        29

<210> SEQ ID NO 71
<211> LENGTH: 22
<212> TYPE: DNA
<213> ORGANISM: Artificial Sequence
<220> FEATURE:
<223> OTHER INFORMATION: Other Information: Primer

<400> SEQUENCE: 71
aggtttcctc tggtcctggt at                                              22

<210> SEQ ID NO 72
<211> LENGTH: 21
<212> TYPE: DNA
<213> ORGANISM: Artificial Sequence
<220> FEATURE:
<223> OTHER INFORMATION: Other Information: Primer

<400> SEQUENCE: 72
gccactgaca accacccta a                                                21

<210> SEQ ID NO 73
<211> LENGTH: 24
<212> TYPE: DNA
<213> ORGANISM: Artificial Sequence
<220> FEATURE:
<223> OTHER INFORMATION: Other Information: Primer
```

```
<400> SEQUENCE: 73
ggaaggaaat tgcgtgtgg agta                                              24

<210> SEQ ID NO 74
<211> LENGTH: 26
<212> TYPE: DNA
<213> ORGANISM: Artificial Sequence
<220> FEATURE:
<223> OTHER INFORMATION: Other Information: Primer

<400> SEQUENCE: 74
gtcgaaaagt gtttctgtca tccaaa                                           26

<210> SEQ ID NO 75
<211> LENGTH: 20
<212> TYPE: DNA
<213> ORGANISM: Artificial Sequence
<220> FEATURE:
<223> OTHER INFORMATION: Other Information: Primer

<400> SEQUENCE: 75
cagatagcga tggtgagcag                                                  20

<210> SEQ ID NO 76
<211> LENGTH: 21
<212> TYPE: DNA
<213> ORGANISM: Artificial Sequence
<220> FEATURE:
<223> OTHER INFORMATION: Other Information: Primer

<400> SEQUENCE: 76
gggatgtgat gagaggtgga t                                                21

<210> SEQ ID NO 77
<211> LENGTH: 23
<212> TYPE: DNA
<213> ORGANISM: Artificial Sequence
<220> FEATURE:
<223> OTHER INFORMATION: Other Information: Primer

<400> SEQUENCE: 77
ccatcctcac catcatcaca ctg                                              23

<210> SEQ ID NO 78
<211> LENGTH: 20
<212> TYPE: DNA
<213> ORGANISM: Artificial Sequence
<220> FEATURE:
<223> OTHER INFORMATION: Other Information: Primer

<400> SEQUENCE: 78
ggctcctgac ctggagtctt                                                  20

<210> SEQ ID NO 79
<211> LENGTH: 23
<212> TYPE: DNA
<213> ORGANISM: Artificial Sequence
<220> FEATURE:
<223> OTHER INFORMATION: Other Information: Primer

<400> SEQUENCE: 79
catcttgggc ctgtgttatc tcc                                              23

<210> SEQ ID NO 80
<211> LENGTH: 22
```

```
<212> TYPE: DNA
<213> ORGANISM: Artificial Sequence
<220> FEATURE:
<223> OTHER INFORMATION: Other Information: Primer

<400> SEQUENCE: 80
cgcttcttgt cctgcttgct ta                                              22

<210> SEQ ID NO 81
<211> LENGTH: 28
<212> TYPE: DNA
<213> ORGANISM: Artificial Sequence
<220> FEATURE:
<223> OTHER INFORMATION: Other Information: Primer

<400> SEQUENCE: 81
tcctatcctg agtagtggta atctactg                                        28

<210> SEQ ID NO 82
<211> LENGTH: 20
<212> TYPE: DNA
<213> ORGANISM: Artificial Sequence
<220> FEATURE:
<223> OTHER INFORMATION: Other Information: Primer

<400> SEQUENCE: 82
gcacctcaaa gctgttccgt                                                 20

<210> SEQ ID NO 83
<211> LENGTH: 22
<212> TYPE: DNA
<213> ORGANISM: Artificial Sequence
<220> FEATURE:
<223> OTHER INFORMATION: Other Information: Primer

<400> SEQUENCE: 83
caagggtggt tgggagtaga tg                                              22

<210> SEQ ID NO 84
<211> LENGTH: 33
<212> TYPE: DNA
<213> ORGANISM: Artificial Sequence
<220> FEATURE:
<223> OTHER INFORMATION: Other Information: Primer

<400> SEQUENCE: 84
acgatggaca actgtctcat atagattttg gac                                  33

<210> SEQ ID NO 85
<211> LENGTH: 33
<212> TYPE: DNA
<213> ORGANISM: Artificial Sequence
<220> FEATURE:
<223> OTHER INFORMATION: Other Information: Primer

<400> SEQUENCE: 85
atgagacagt tgtccatcgt ctttcaccat gat                                  33

<210> SEQ ID NO 86
<211> LENGTH: 32
<212> TYPE: DNA
<213> ORGANISM: Artificial Sequence
<220> FEATURE:
<223> OTHER INFORMATION: Other Information: Primer

<400> SEQUENCE: 86
```
ggatcacaag aagaaaaatt ttggttataa ac                                         32

<210> SEQ ID NO 87
<211> LENGTH: 32
<212> TYPE: DNA
<213> ORGANISM: Artificial Sequence
<220> FEATURE:
<223> OTHER INFORMATION: Other Information: Primer

<400> SEQUENCE: 87
aatttttctt cttgtgatcc aaaaagtgtc ca                                         32

<210> SEQ ID NO 88
<211> LENGTH: 33
<212> TYPE: DNA
<213> ORGANISM: Artificial Sequence
<220> FEATURE:
<223> OTHER INFORMATION: Other Information: Primer

<400> SEQUENCE: 88
gtgccatttg gtttgacaca ggatttctta ata                                        33

<210> SEQ ID NO 89
<211> LENGTH: 33
<212> TYPE: DNA
<213> ORGANISM: Artificial Sequence
<220> FEATURE:
<223> OTHER INFORMATION: Other Information: Primer

<400> SEQUENCE: 89
tgtgtcaaac caaatggcac acgttctcgt tta                                        33

<210> SEQ ID NO 90
<211> LENGTH: 33
<212> TYPE: DNA
<213> ORGANISM: Artificial Sequence
<220> FEATURE:
<223> OTHER INFORMATION: Other Information: Primer

<400> SEQUENCE: 90
gtgccattta ttttgacaca ggatttctta ata                                        33

<210> SEQ ID NO 91
<211> LENGTH: 33
<212> TYPE: DNA
<213> ORGANISM: Artificial Sequence
<220> FEATURE:
<223> OTHER INFORMATION: Other Information: Primer

<400> SEQUENCE: 91
tgtgtcaaaa taaatggcac acgttctcgt tta                                        33

<210> SEQ ID NO 92
<211> LENGTH: 32
<212> TYPE: DNA
<213> ORGANISM: Artificial Sequence
<220> FEATURE:
<223> OTHER INFORMATION: Other Information: Primer

<400> SEQUENCE: 92
atagtgatta gtgaaggagc ccaagaatgc ac                                         32

<210> SEQ ID NO 93
<211> LENGTH: 32
<212> TYPE: DNA
<213> ORGANISM: Artificial Sequence

```
<220> FEATURE:
<223> OTHER INFORMATION: Other Information: Primer

<400> SEQUENCE: 93
gctccttcac taatcactat taagaaatcc tg                                32

<210> SEQ ID NO 94
<211> LENGTH: 33
<212> TYPE: DNA
<213> ORGANISM: Artificial Sequence
<220> FEATURE:
<223> OTHER INFORMATION: Other Information: Primer

<400> SEQUENCE: 94
gacaccttta ggatcacaag aagaaaaaat ttg                               33

<210> SEQ ID NO 95
<211> LENGTH: 33
<212> TYPE: DNA
<213> ORGANISM: Artificial Sequence
<220> FEATURE:
<223> OTHER INFORMATION: Other Information: Primer

<400> SEQUENCE: 95
cttgtgatcc taaaagtgtc caaaatctat atg                               33

<210> SEQ ID NO 96
<211> LENGTH: 33
<212> TYPE: DNA
<213> ORGANISM: Artificial Sequence
<220> FEATURE:
<223> OTHER INFORMATION: Other Information: Primer

<400> SEQUENCE: 96
gcgccatttg ttttgacaca ggatttctta ata                               33

<210> SEQ ID NO 97
<211> LENGTH: 33
<212> TYPE: DNA
<213> ORGANISM: Artificial Sequence
<220> FEATURE:
<223> OTHER INFORMATION: Other Information: Primer

<400> SEQUENCE: 97
tgtgtcaaaa caaatggcgc acgttctcgt tta                               33

<210> SEQ ID NO 98
<211> LENGTH: 32
<212> TYPE: DNA
<213> ORGANISM: Artificial Sequence
<220> FEATURE:
<223> OTHER INFORMATION: Other Information: Primer

<400> SEQUENCE: 98
aaaatcactg agcaggagaa agattttcta tg                                32

<210> SEQ ID NO 99
<211> LENGTH: 33
<212> TYPE: DNA
<213> ORGANISM: Artificial Sequence
<220> FEATURE:
<223> OTHER INFORMATION: Other Information: Primer

<400> SEQUENCE: 99
ttctcctgct cagtgatttt agagagaggg atc                               33
```

```
<210> SEQ ID NO 100
<211> LENGTH: 32
<212> TYPE: DNA
<213> ORGANISM: Artificial Sequence
<220> FEATURE:
<223> OTHER INFORMATION: Other Information: Primer

<400> SEQUENCE: 100
gaaatcacta agcaggagaa agattttcta tg                                    32

<210> SEQ ID NO 101
<211> LENGTH: 33
<212> TYPE: DNA
<213> ORGANISM: Artificial Sequence
<220> FEATURE:
<223> OTHER INFORMATION: Other Information: Primer

<400> SEQUENCE: 101
ttctcctgct tagtgatttc agagagaggg atc                                   33

<210> SEQ ID NO 102
<211> LENGTH: 32
<212> TYPE: DNA
<213> ORGANISM: Artificial Sequence
<220> FEATURE:
<223> OTHER INFORMATION: Other Information: Primer

<400> SEQUENCE: 102
caaatgaatg atgcacgtca tggtggctgg ac                                    32

<210> SEQ ID NO 103
<211> LENGTH: 33
<212> TYPE: DNA
<213> ORGANISM: Artificial Sequence
<220> FEATURE:
<223> OTHER INFORMATION: Other Information: Primer

<400> SEQUENCE: 103
tgacgtgcat cattcatttg tttcatgaaa tac                                   33
```